US008474978B2

(12) United States Patent
Huang et al.

(10) Patent No.: US 8,474,978 B2
(45) Date of Patent: Jul. 2, 2013

(54) PATTERN ANALYSIS OF RETINAL MAPS FOR THE DIAGNOSIS OF OPTIC NERVE DISEASES BY OPTICAL COHERENCE TOMOGRAPHY

(75) Inventors: David Huang, Pasadena, CA (US); Ou Tan, Pasadena, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 12/139,376

(22) Filed: Jun. 13, 2008

(65) Prior Publication Data

US 2008/0309881 A1 Dec. 18, 2008

Related U.S. Application Data

(60) Provisional application No. 60/944,449, filed on Jun. 15, 2007.

(51) Int. Cl.
*A61B 3/12* (2006.01)
*A61B 3/10* (2006.01)

(52) U.S. Cl.
CPC .. *A61B 3/102* (2013.01); *A61B 3/12* (2013.01)
USPC ........................................................ 351/246

(58) Field of Classification Search
CPC .................................. A61B 3/102; A61B 3/12
USPC .............. 351/246, 206–207, 221; 359/216.1, 359/201.1
See application file for complete search history.

(56) References Cited

U.S. PATENT DOCUMENTS

| 6,104,828 | A | * | 8/2000 | Shioiri ........................ 351/206 |
| 7,301,644 | B2 | | 11/2007 | Knighton et al. |
| 7,347,548 | B2 | | 3/2008 | Huang et al. |
| 7,364,296 | B2 | | 4/2008 | Miller et al. |
| 2003/0135122 | A1 | | 7/2003 | Bambot et al. |
| 2005/0018133 | A1 | | 1/2005 | Huang et al. |
| 2006/0058682 | A1 | | 3/2006 | Miller et al. |
| 2006/0119858 | A1 | | 6/2006 | Knighton et al. |
| 2006/0187462 | A1 | * | 8/2006 | Srinivasan et al. ............ 356/479 |
| 2007/0216909 | A1 | * | 9/2007 | Everett et al. ................. 356/479 |

OTHER PUBLICATIONS

Leung, Christopher KS, Wai-Man Chan, Wing-Ho Yung, Alan CK Ng, Jackson Woo, Moon-Kong Tsang, and Raymond KK Tse. "Comparison of Macular and Peripapillary Measurements for the Detection of Glaucoma." Ophthalmology 112.3 (2005): 391-400.*
Schuman, Joel S., Michael R. Hee, Carmen A. Puliafito, Carlton Wong, Tamar Pedut-Kloizman, Charles P. Lin, Ellen Hertzmark, Joseph A. Izatt, Eric A. Swanson, and James G. Fujimoto. "Qunatification of Nerve Fiber Layer Thickness in Normal and Glaucomatous Eyes Using Optical Coherence Tomography." Arch Ophthalmology 113 (1995): 586-596. Print.*

(Continued)

*Primary Examiner* — Zachary Wilkes
(74) *Attorney, Agent, or Firm* — DLA Piper LLP (US)

(57) ABSTRACT

Methods for analyzing retinal tomography maps to detect patterns of optic nerve diseases such as glaucoma, optic neuritis, anterior ischemic optic neuropathy are disclosed in this invention. The areas of mapping include the macula centered on the fovea, and the region centered on the optic nerve head. The retinal layers that are analyzed include the nerve fiber, ganglion cell, inner plexiform and inner nuclear layers and their combinations. The overall retinal thickness can also be analyzed. Pattern analysis are applied to the maps to create single parameter for diagnosis and progression analysis of glaucoma and optic neuropathy.

15 Claims, 20 Drawing Sheets

OTHER PUBLICATIONS

Budenz, Donald L., Robert T. Chang, Xianrun Huang, Robert W. Knighton, and James M. Tielsch. "Reproducibility of Retinal Nerve Fiber Thickness Measurements Using the Stratus OCT in Normal and Glaucomatous Eyes." Investigative Ophthalmology and Visual Science 46.7 (2005): 2440-2443. Print.*

International Search Report for corresponding PCT application PCT/US2008/066987 lists the references above.

Tan, Ou et al., "Mapping of Macular Substructures With Optical Coherence Tomography for Glaucoma Diagnosis", Ophthalmology 2008;115(6):949-956.

Ishikawa, Hiroshi et al., "Macular Segmentation with Optical Coherence Tomography", Investigative Ophthalmology & Visual Science 2005;46(6):2012-2017.

Wollstein, Gadi et al., "Optical Coherence Tomography (OCT) Macular and Peripapillary Retinal Nerve Fiber Layer Measurements and Automated Visual Fields", Am J Ophthalmol 2004;138(2):218-225.

Guedes, Viviane et al., "Optical Coherence Tomography Measurement of Macular and Nerve Fiber Layer Thickness in Normal and Glaucomatous Human Eyes", Ophthalmology 2003;110(1)177-189.

Zeimer, Ran et al., "Quantitative Detection of Glaucomatous Damage at the Posterior Pole by Retinal Thickness Mapping. A Pilot Study", Ophthalmology 1998;105(2):224-231.

Watanabe, Yuuki et al., "Quasi-single Shot Axial-lateral Parallel Time Domain Optical Coherence Tomography With Hilbert Transformation", Opt Express 2008;16(2):524-534.

* cited by examiner

PATTERN ANALYSIS OF RETINAL MAPS FOR THE DIAGNOSIS OF OPTIC NERVE DISEASES BY OPTICAL COHERENCE TOMOGRAPHY

CROSS-REFERENCE TO RELATED APPLICATIONS

This application claims the benefit of U.S. Provisional Application No. 60/944,449 filed Jun. 15, 2007, entitled "PATTERN ANALYSIS OF RETINAL MAPS FOR THE DIAGNOSIS OF OPTIC NERVE DISEASES BY OPTICAL COHERENCE TOMOGRAPHY". The benefit under 35 USC §119(e) of the United States provisional application is hereby claimed. The above priority application is hereby incorporated herein by reference.

STATEMENT REGARDING FEDERALLY SPONSORED RESEARCH AND DEVELOPMENT

The present invention is made, at least in part, with the support of NIH grant R01 EY013516. The government has certain rights in the invention.

FIELD OF THE INVENTION

The invention pertains to the field of ophthalmology. More particularly, the invention pertains to methods for acquiring and analyzing optical coherence tomography images to detect optic nerve diseases.

BACKGROUND OF THE INVENTION

All optic neuropathies primarily affect the inner layers of the retina. In particular, the nerve fiber layer (NFL), the ganglion cell layer (GCL) and the inner plexiform layer (IPL) are most affected. In contrast, the inner nuclear layer (INL) is less affected and the outer layers are not affected [1]. Because each of the 3 inner layers of the retina contain different parts of the retinal ganglion cells (NFL contains the axons, GCL contains the cell bodies, and IPL contains the dendrites), diagnostic methods that take this local anatomical variation into account will generally have better diagnostic specificity. For instance, although measurements of the overall retinal thickness will provide general diagnostic information, measurements that focus around the area nearby the optic nerve head (ONH, also called optic disc) will provide much more diagnostic information because the NFL is thickest in this area. In the macula (area around the fovea), all 3 inner layers contributes diagnostic information, therefore, it is best to measure the combined Inner Retinal Layers that include the NFL, GCL and IPL.

While this principle is simple in theory, it is not easy in practice. Take the diagnosis of glaucoma for example. Glaucomatous optic neuropathy is a result of several progressive alterations in ocular anatomy: loss of retinal ganglion cells (RGCs), thinning of the retinal nerve fiber layer (NFL), and cupping of the optic disc. Thus, it stands to reason that these anatomical changes can be used as diagnostic indicators for glaucoma. Unfortunately, in practice, this knowledge cannot be easily utilized in diagnostic methods. RGC loss cannot be seen on conventional slit-lamp ophthalmic examinations. Likewise, NFL bundle defects are difficult to detect on clinical examination. Although red-free fundus photography is capable of detecting changes in the vascular system and nerve fibers of the retina, the technique is rarely used in clinical practice. Thus, clinical diagnosis of glaucoma is currently based only on characteristic optic nerve cupping in conjunction with tests for the corresponding visual field deficits in the patient.

However, since a significant loss to RGC population can occur prior to detectable visual field deficits, and this structural loss can precede detectable function loss by up to 5 years, current methods for clinical diagnosis of glaucoma are not adequate for early detection of the disease. Thus, there currently exists an unmet need for detection and prognostication methods that are capable of identifying and quantifying changes in the RGC population which are also easy to administer in clinical settings.

SUMMARY OF THE INVENTION

Briefly, the present invention provides a method for detecting and diagnosing optical neuropathies in a subject, which includes the general steps of generating a macular map using FD-OCT; constructing a three-dimensional thickness map of the macular region based on the macular map; computing a derivative map from the thickness map; identifying abnormal areas in the map(s) by applying a pattern analysis method to the map(s); and determining a diagnostic parameter based on the thickness map, the derivative map, the identified abnormal areas in the map(s), or a combination thereof.

In the methods of the present invention, the inventors have discovered that the quality of the macular maps and the subsequent construction of the thickness maps are highly dependent on the scanning patterns employed. Accordingly, inventors of the present invention have devised novel scanning patterns for achieving rapid macular scans that can facilitate the construction of high quality three-dimensional thickness maps.

Once a macular map is obtained by employing a scanning pattern in accordance with embodiments of the present invention, a two-dimensional thickness map of the macular area may then be constructed by interpolating between the individual scans of the macular map. From this two-dimensional map of the macular region, various derivative maps may then be constructed and pattern analysis methods applied to extract diagnostic information useful for detecting and diagnosing optic neuropathies.

Figure 1:
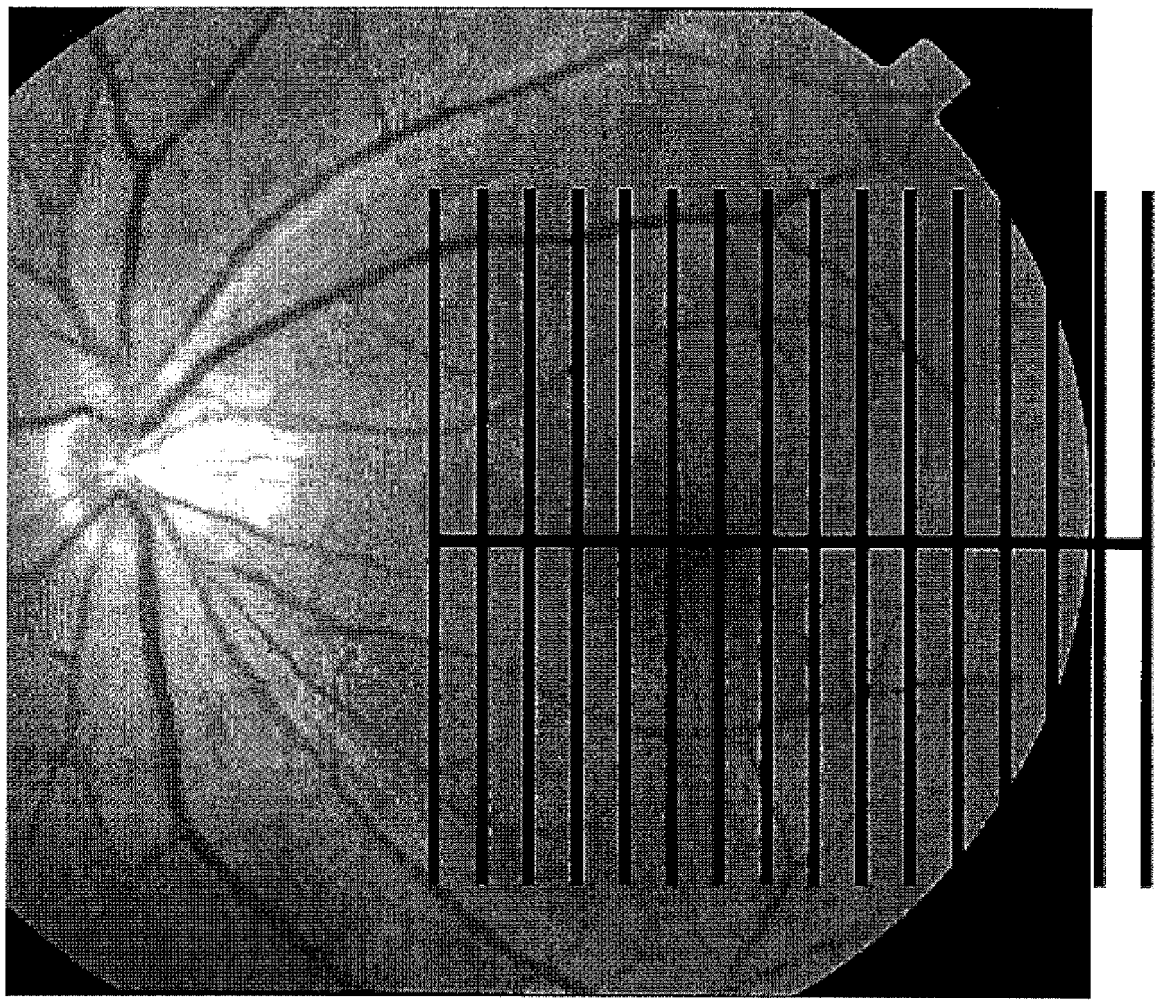
FIG. 1 illustrates the Macular Map 7-mm (MM7) scanning pattern in accordance with embodiments of the present invention. The exemplary scan shown in the figure scanned 14,944 points in a 7 mm square area within 0.58 seconds.

In a preferred embodiment, FD-OCT images of a subject's macular region is first acquired by executing a series of cross-sectional scans according to the MM7 scanning pattern as shown in FIG. 1. This first set of raw cross-sectional scans are then processed and interpolated to construct a three-dimensional model of the patient's macular region. From this three dimensional model, retinal thickness map and other derivative maps can then be computed. Preferably, a fractional deviation map is computed from the thickness map and areas of abnormal retinal thickness are identified. Using these maps, diagnostic parameters are then computed. Preferably, the parameter focal loss volume (FLV) and global loss volume (GLV), as defined in the detailed description below, are computed and used to aid the determination of a diagnosis.

While the above described embodiment outlines the general steps of the present invention, it will be understood by those skilled in the art that various modifications are possible. Other aspects and advantages of the present invention will become apparent from the following detailed description and the appended claims.

DETAILED DESCRIPTION

As set forth above, the present invention describes methods for acquiring diagnostic images of the macula and the subsequent analysis of the images to yield diagnostic parameters that are useful for making diagnosis. In particular, the prevent invention provides methods for generating macular maps (images) using non-invasive imaging techniques such as the FD-OCT, and methods for processing and analyzing the generated maps (images). By measuring and monitoring changes in the anatomical structures around the macular region at a high resolution, pathological conditions may be detected at earlier stages even before the manifestation of disease symptoms. Methods of the present invention are applicable to all types of optic neuropathies that affect the macular region.

In general, optic neuropathy detection and diagnosis methods in accordance with embodiments of the present invention will have the steps of: generating an initial map centered on the fovea (macular map) or the optic nerve head (peripapillary map) using Fourier-domain optical coherence tomography (FD-OCT), wherein said initial map consists of a scanning pattern formed by a plurality of cross-sectional scans; constructing a map of a retinal property based on the initial map; computing a derivative map from the map of the retinal property; applying a pattern analysis method to the map of the retinal property or the derivative map to detect abnormal areas; and; determining a diagnostic parameter based on the maps, derivative map, detected abnormal areas, or a combination thereof, wherein said diagnostic parameter, thickness map and the derivative map can each be used alone or in combination to diagnose and differentiate different types of optic neuropathies.

The scanning pattern used for generating the macular map is preferably one that covers a wide area of the macula. The resulting macular map should preferably have a resolution of at least 10 μm. The scanning should preferably be completed within about 2 seconds. In one preferred embodiment, the scanning pattern is the MM7 pattern as shown in FIG. 1.

The thickness map is constructed from the raw macular map comprised of a plurality of cross-sectional images of the macula. By aligning each of the neighboring cross-sectional scans and interpolating between the cross-sections, a three-dimensional image of the macula may be obtained from the collection of 2-dimensional axial scans in the macular map. By identifying structural boundaries in the image and measuring the distances and sizes of the anatomical structures, thicknesses of the retinal layers may be assigned to arrive at a thickness map. Depending on the structure of interest, various thickness maps may be constructed, including, total retinal thickness, ganglion cell complex (or inner retinal layer) thickness, nerve fiber layer thickness, ganglion cell layer thickness, inner plexiform layer thickness, but are not limited thereto.

Construction of the thickness map is preferably automated by software, but it may also be done manually.

The property map may further be restricted to a particular spatial location of the retina, for example, the peripapillary region (area near the optic disk).

Once the property maps are constructed, a wide variety of derivative maps may be obtained by applying a data transformation algorithm to the property maps. Exemplary derivative maps may include deviation map, fractional deviation map, pattern deviation map, or a combination thereof, but not limited thereto.

To detect areas of abnormality in the maps, a variety of pattern analysis algorithms may be applied to the property maps or the derivative maps. The pattern analysis algorithms are preferably statistically based algorithms. Exemplary statistical pattern analysis algorithms of the present invention may include standard deviation comparison, overall average, superior average, inferior average, or a combination thereof, but are not limited thereto. Selection of the pattern analysis algorithm will depend on the object of analysis.

Once the areas of abnormality have been identified, diagnostic parameters may be defined and computed from the maps and knowledge of the abnormal areas. Exemplary diagnostic parameters may include focal loss volume (FLV), global loss volume (GLV), pattern coefficient of variation (PCV) or (glaucoma) pattern cross-correlation (GPCC), but are not limited thereto.

The diagnostic parameters are useful either alone or in conjunction with other parameters in making diagnosis determinations. Examples of optic neuropathies that are applicable to methods of the present invention may include glaucoma, optic neuritis, anterior ischemic optic neuropathy (AION), but are not limited thereto.

When the maps are cross-correlated to other maps characteristic of certain optic neuropathies, a cross-correlation parameter may be computed. A higher cross-correlation between the test subject's map to a disease reference map indicates a higher likelihood that the subject may suffer from the disease.

To further illustrate the operating principles and benefits of the present invention, we will first consider the diagnosis of glaucoma.

As discussed in the background, one of the defining characteristics of glaucoma is the loss of RGC. It is known in the art that a significant proportion of RGC population resides in the macula, thus, macula thickness provides a useful diagnostic measure for detecting and prognosticating glaucoma. Reduced macular thickness in glaucoma was initially described by Zeimer et al (ref 6) using the slit-scanning Retinal Thickness Analyzer (RTA, Talia Technology Ltd., Neve-Ilan, Israel). Since the introduction of optical coherence tomography (OCT) by one of the inventors of this invention (Huang) and his co-workers, the technology has proven to be useful for measuring circumpapillary nerve fiber layer thickness (cpNFLT) which was shown to be a useful parameter for detecting glaucoma. However, total macular retinal thickness (mRT) measurement using OCT has not been as accurate a diagnostic parameter as cpNFLT. The earlier retinal OCT systems employed the slower time-domain technology (TD), which can only provide a few cross-section image of the retina within a few seconds. For instance, the Stratus OCT system (Carl Zeiss Meditec, Inc., Dublin, Calif.) can only scan 6 meridianal cross-sections of the macula within 2 seconds which results in a low resolution map of retinal thickness. Such low resolution maps are inadequate for accurate diagnostic purposes.

Recently, a new generation of retinal OCT systems utilizing the Fourier domain optical coherence tomography (FD-OCT) technology has become available. FD-OCT is much faster than TD-OCT. For example, the RTVue FD-OCT system (Optovue, Inc., Fremont, Calif.) is 65 times faster than the Stratus TD-OCT. The much higher scan speed of FD-OCT allows higher density retinal mapping over a larger area in a shorter period of time. The shorter scan time reduce motion error and the higher density and scan area permit more detailed pattern analysis.

However, the faster scanning speed of FD-OCT does not directly translate into more accurate diagnosis. Without proper methods to decipher the scanned images, the potential of this new technology cannot be fully exploited. In view of the unmet needs I the art and the un-bridged technical gap, inventors of the present invention have devised novel OCT scanning patterns and analysis methods to realize the potential of FD-OCT in accurately measuring retinal thickness and diagnosing optical neuropathies.

In general, methods in accordance with embodiments of the present invention will have the stages of (1) image acquisition; (2) image processing, transformation, and analysis; (3) diagnostic parameter computation; and (4) diagnosis determination.

Because methods of present invention is based on non-invasive imaging technologies, it is expected that they are not limited to human, but are also applicable to animals other than human. Accordingly, the term "subject" as used herein broadly refers to any organism with an eye or eyes similar to human eyes. It will be understood by one of ordinary skill in the art that any organism having an eye or eyes with anatomical structures similar to the human eyes may be considered applicable subject in methods of the present invention.

1. Image Acquisition

During the first stage, a non-invasive imaging technique is preferably used to generate an initial image of the macular region or the peripapillary region of the subject's eye(s). Here the macular region is centered on the fovea and the peripapillary region is centered on the optic nerve head. Suitable imaging technologies must be able to image the regions at a sufficiently high resolution and speed so that the resulting images will have sufficient quality for diagnostic purposes. Preferably, the technique should be able to image an area no smaller than about 6 mm×6 mm in macula or 4 mm×4 mm at optic disc, and at a speed no slower than about 2 seconds per image. In some preferred embodiments, FD-OCT is used to generate the initial macular map.

It will be understood by those skilled in the art that while exemplary embodiments described herein are based on FD-OCT, other imaging technologies, including future developed imaging technologies, may also be used so long as the technologies are capable of generating images meeting the criteria set forth herein. For example, a new type of TD-OCT employing a two-dimensional array of detectors working in parallel to speed up image acquisition such as that described by (ref 7) may potentially be used.

However, when FD-OCT is used as the imaging technology, the present invention further provides novel scanning patterns that are capable of facilitating the acquisition and generation of three-dimensional images. Because OCT images are cross-sectional scan images, construction of a three-dimensional model will require aligning the individual cross-sectional scans and interpolating between the scans to stitch together the final three-dimensional representation. Alignment of the individual scans is a difficult and time consuming task because each scan is taken independent of each other both chronologically and spatially. Misalignment of the cross-sectional scans will result in an inaccurate representation of the macula region, which will limit the diagnostic power of the method.

To solve this problem, the inventors have devised novel scanning patterns that are capable of facilitating rapid and accurate alignments. Referring to FIG. 1, there is shown an exemplary scanning pattern comprising a plurality of vertical scanning lines with one horizontal scanning line crossing the plurality of the vertical scanning lines. The plurality of vertical scanning lines are preferably spaced with equal distance. The horizontal scanning line preferably intersects the plurality of vertical scanning lines at perpendicular angle. This horizontal scanning line provides a common reference point for aligning all the vertical scanning lines, which greatly facilitates the alignment and interpolation process.

To measure macular GCC loss caused by glaucoma, a wider scan pattern, specially in the vertical direction, can help find the loss of ganglion cells in parafovea and perifovea region. As visual field function test cover much wider area than current OCT macular scan pattern, wider OCT scan pattern also help finding the correlation between function loss and structure damage. Comparing with radial scan, grid scan or raster scan can create GCC thickness maps with higher transverse resolution in parafovea and perifovea region.

In the particular embodiment shown in FIG. 1, the scanning pattern is referred to herein as the Macular Map 7-mm (MM7) scan pattern. The FD-OCT image is obtained using the RTVue FD-OCT system. The exemplary scan pattern contains 16 vertical cross-sections and 1 horizontal cross-sections of the retina. However, the number of scanning lines is not particularly limited. Depending on the desired scanning area and resolution, other numbers of scanning lines may also be suitably used.

2. Image Processing, Transformation, and Analysis

In the second stage, the raw image data obtained in the previous stage is further processed to generate a more refined three-dimensional model of the macular region. Depending on the technology used to acquire the raw data, different amount of image processing may be required to transform the raw image data into a format suitable for further analysis. For example, if the imaging technology acquires the raw data in analog format, it is preferred that the data be processed and transformed into digital format to facilitate further analysis.

Figure 2:
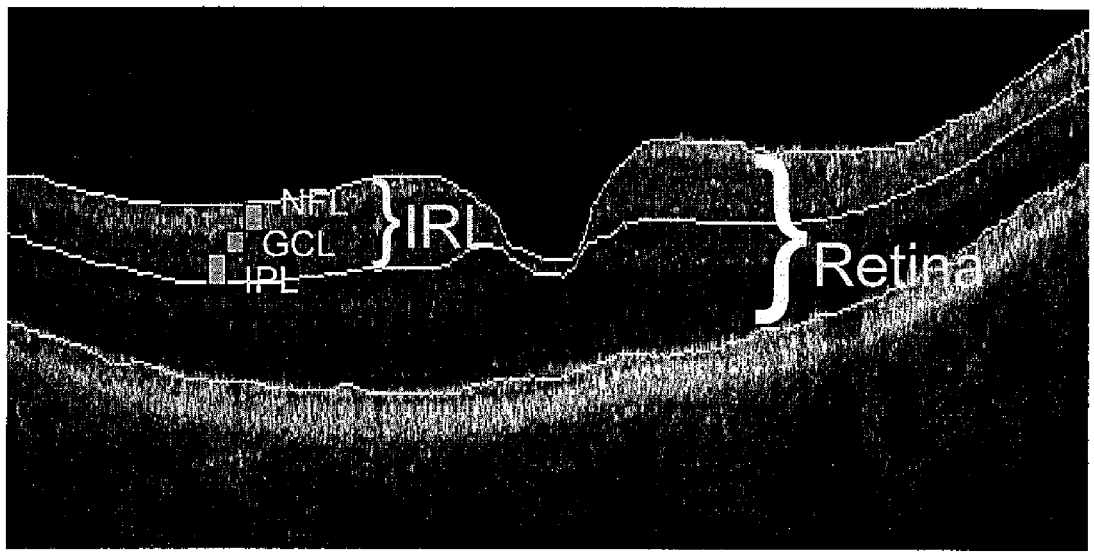
FIG. 2 shows an exemplary OCT image of a cross-section of the retina in the macular region. The Ganglion cell complex (GCC), also called inner retinal layer (IRL), consists of the nerve fiber layer (NFL), ganglion cell layer (GCL) and the inner plexiform layer (IPL). The retina is thinner in the foveal depression, which serves as a landmark for locating the foveal center.

Referring to FIG. 2, there is shown an exemplary cross-sectional image of the retina. This processed image allows measurement of the thickness of the retina and the inner retinal layer. The image processing steps to measure the retina and inner retinal layer thickness are already known to those skilled in this art (see references 1-2, the content of which are incorporated herein by reference). The center of the foveal depression is identified on the vertical and horizontal cross-sections that cross the fovea. The scans are obtained with the subject eye fixated on a visual target. However, the fixation point may deviate slightly from the target. The center of the foveal depression serves as an anatomic landmark on which to center the thickness maps.

Figure 3:
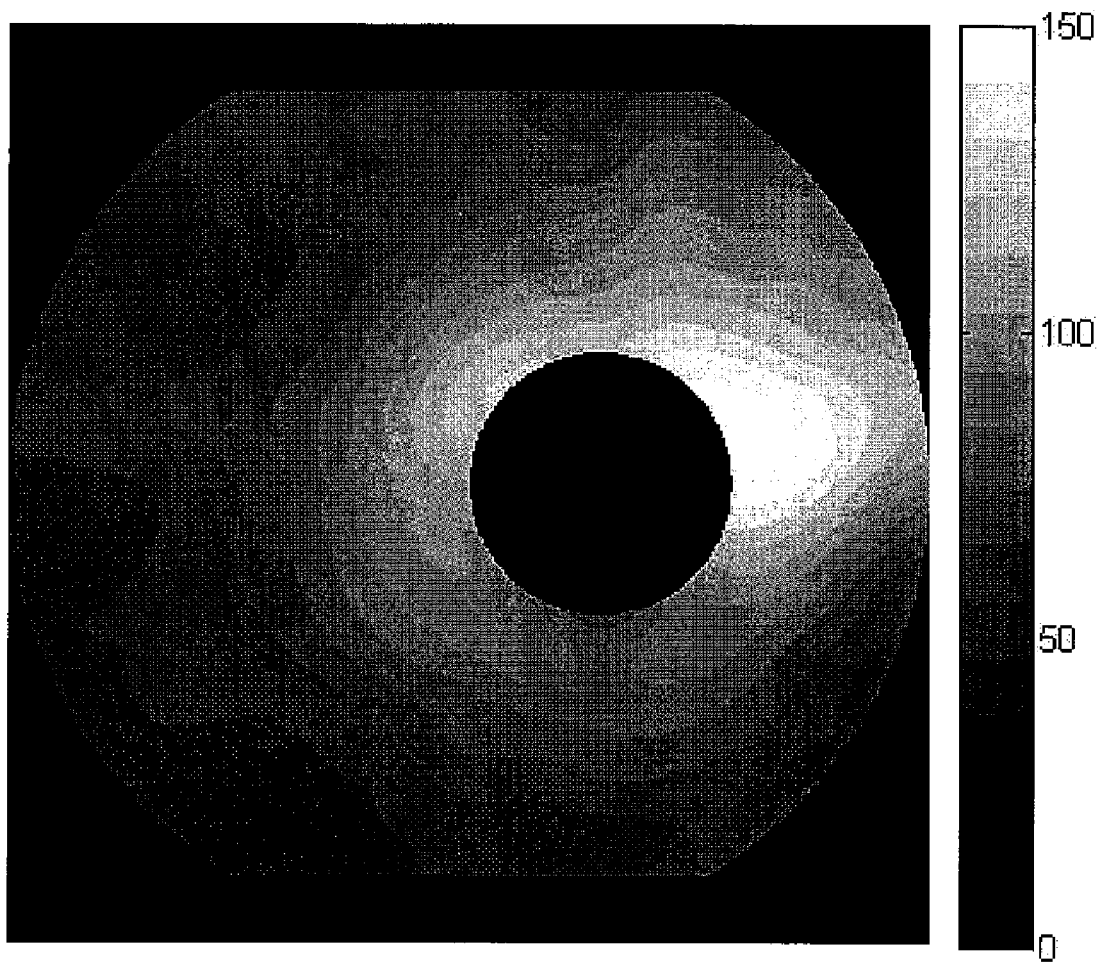
FIG. 3 shows an exemplary GCC thickness map in accordance with embodiments of the present invention. The unit is μm. The central foveal area (black circle) where the GCC cannot be reliably measured is removed from analysis.

In a preferred embodiment wherein the raw data consists of OCT cross-sectional scans of the macular region, an exemplary GCC thickness map (FIG. 3) may be constructed by interpolation between the OCT cross-sections. The map is preferably cropped to preserve only the central 7-mm circular area because measurements are not as reliable in the corner areas. The map is preferably centered on the foveal depression based on the retinal thickness map. As can be seen from FIG. 3, the GCC thickness is very thin or entirely absent in the fovea. Thus the foveal area is removed from further analysis of the GCC. The foveal region could be used if the analysis is done on the entire retinal thickness.

Once the raw image data are processed and placed in a suitable format, various pattern analysis algorithms may be designed and applied to the data to extract a variety of useful information. From these processed image data, diagnostic parameters useful for aiding the diagnosis of disease conditions may be derived.

One exemplary embodiment of the current invention is the measurement of retinal tissue loss within an abnormally thin area of the retina. This parameter is referred to herein as the focal loss volume (FLV). In the following sections, we will first describe one exemplary computation of FLV based on the fractional loss map and pattern deviation map of the macular GCC. We will then further describe alternative embodiments of the invention.

Fractional Deviation Map

In one preferred embodiment, a novel derivative map, herein referred to as a "fractional deviation map", is computed from the GCC thickness map. To compute the fractional deviation map, a normative reference is required.

In an exemplary embodiment, 46 normal subjects in the Advanced Imaging for Glaucoma Study (AIGS) were used as the normative reference. It will be understood by those skilled in the art that this is a statistical procedure and that other suitable data set may also be used.

Figure 4:
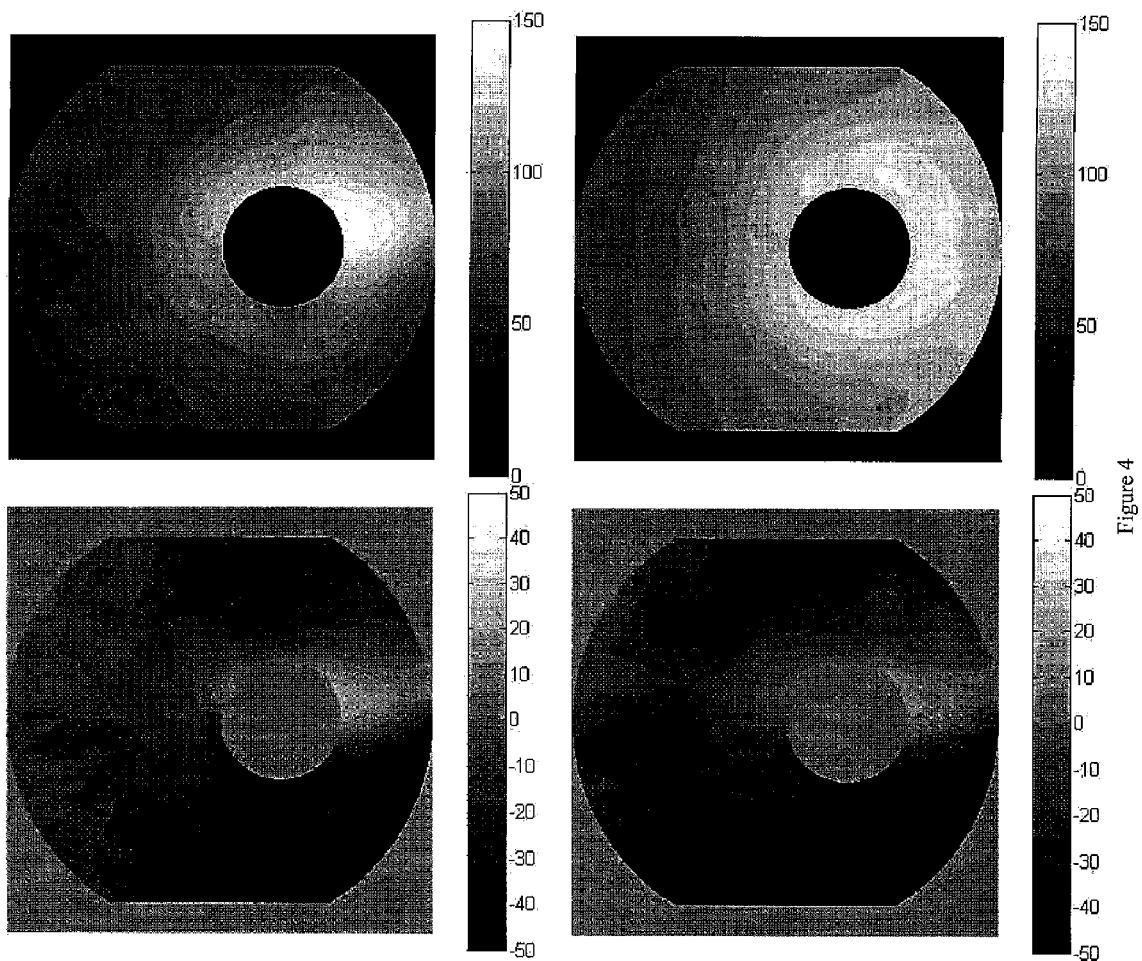
FIG. 4 shows a set of exemplary GCC thickness maps and derivative maps in accordance with embodiments of the present invention. Upper left: GCC thickness map of the eye being tested, unit:μm. Upper right: normal mean GCC thickness map, unit:μm. Lower left: deviation (D) map, unit:μm. Lower right: fractional deviation (FD) map, unit:%.

The subject recruitment and testing procedures are defined in the AIGS Manual of Procedures (MOP) available on the AIG study website [3]. GCC thickness maps are measured from a group of normal eyes that do not have glaucoma, optic nerve disease or retinal disease. The GCC thickness maps of the normal reference population are averaged to obtain the normal mean map (FIG. 4).

The deviation (D) map is then computed by subtracting the GCC map being tested by the normal mean map.

$$D\_map = Map - Normal\_mean\_map$$

The fractional deviation (FD) map is computed by dividing the D map by the normal mean map.

$$FD\_map = D\_map / Normal\_mean\_map$$

3. Diagnostic Parameter Computation

In the third stage, a diagnostic parameter is defined and computed from the image data obtained in the first two stages. As mentioned above, various diagnostic parameters may be defined and computed to aid the diagnosis of disease conditions. In a preferred embodiment, the focal loss volume (FLV) parameter is computed.

Figure 5:
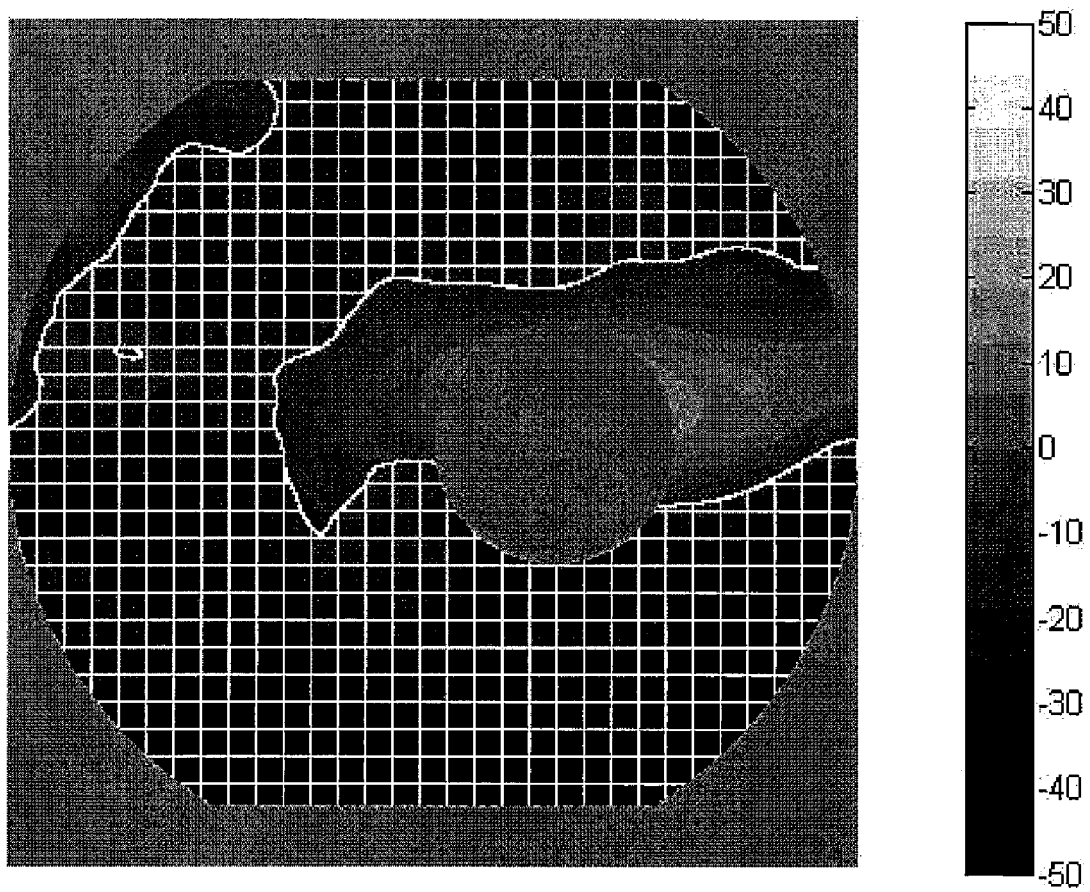
FIG. 5 shows an exemplary GCC FD map of a glaucomatous eye with areas of statistically significant focal loss marked by the hatch pattern. The unit is %.

Preferably, areas of abnormal GCC thinning are detected using a statistical criterion. One exemplary criterion is to detect thinning to below 5 percentile of the normal sample population. Point-by-point statistical calculation was performed on the FD maps of the normal population to obtain the standard deviation (SD) map. Values below 5 percentile of normal distribution (mean−1.64 SD) are considered to be significantly abnormal. The area of abnormal thinning could be computed from the GCC thickness, D, or FD maps and the results are exactly the same. In one exemplary embodiment, the abnormal areas of focal loss are identified on the FD map (FIG. 5) and the FD values in the abnormal area are summed (area integral) to obtain the focal loss volume (FLV). When FLV is totally defined by FD, it is called FD-FLV. Preferably the FD-FLV is normalized by dividing the map area so FD-FLV can be expressed as a percentage. Thus an FD_FLV of 9% would indicate a 9% loss of ganglion cells.

Although the FD-FLV example above is computed from the GCC thickness FD map, those skilled in the art will recognize that it can also be computed from the D map. Other types of maps such as reflectance map and peripapillary NFL map could also be used as a basis for computing FD-FLV. Computing the FLV from the PD map is less straight forward but provides the best diagnostic power.

We briefly describe these alternative embodiments below.
Pattern Deviation Focal Loss Volume (PD_FLV)

In one alternative embodiment, another exemplary diagnostic parameter referred to herein as the pattern deviation focal loss volume (PD_FLV) may be used. It's computation is described as follows.

1. Deriving the Pattern Deviation Map

Figure 6:
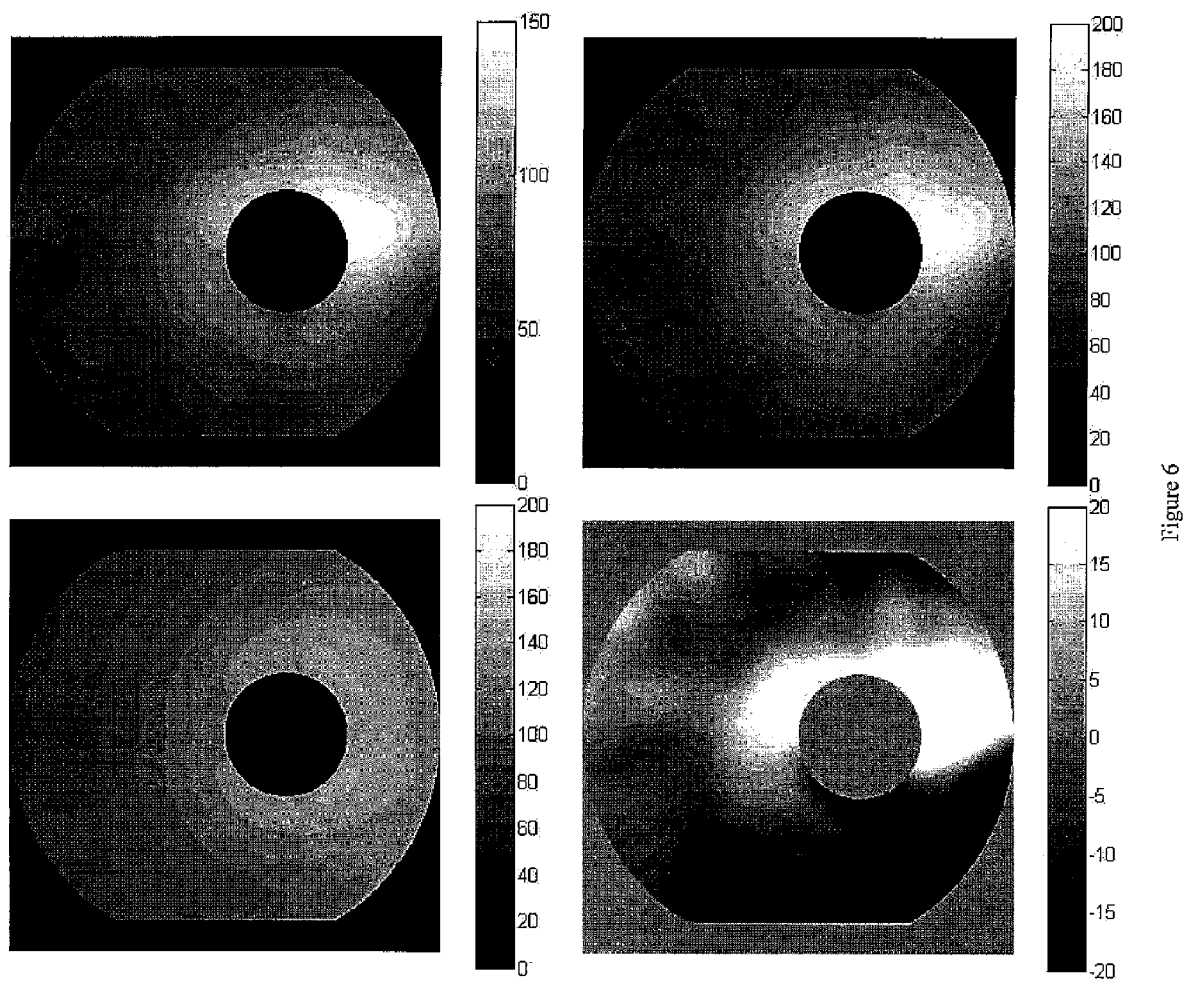
FIG. 6 shows a set of exemplary GCC thickness maps and derivative maps. Upper left: GCC thickness map of the eye being tested, unit:μm. Upper right: pattern map of the test eye, unit %. Lower left: pattern map of the average normal eye, unit %. Lower right: pattern deviation (PD) map, unit %.

The pattern map is derived from the GCC thickness map by dividing the map by its average value (FIG. 6).

$$Pattern\_map = Map/Average$$

The pattern map of the eye being tested is then subtracted by the average pattern map of the normal reference population to obtain the pattern deviation (PD) map (FIG. 6).

$$PD\_map = Pattern\_map - Normal\_mean\_pattern\_map$$

2. Computing the Pattern Deviation Volume Focal Loss Volume (PD_FLV)

Figure 7:
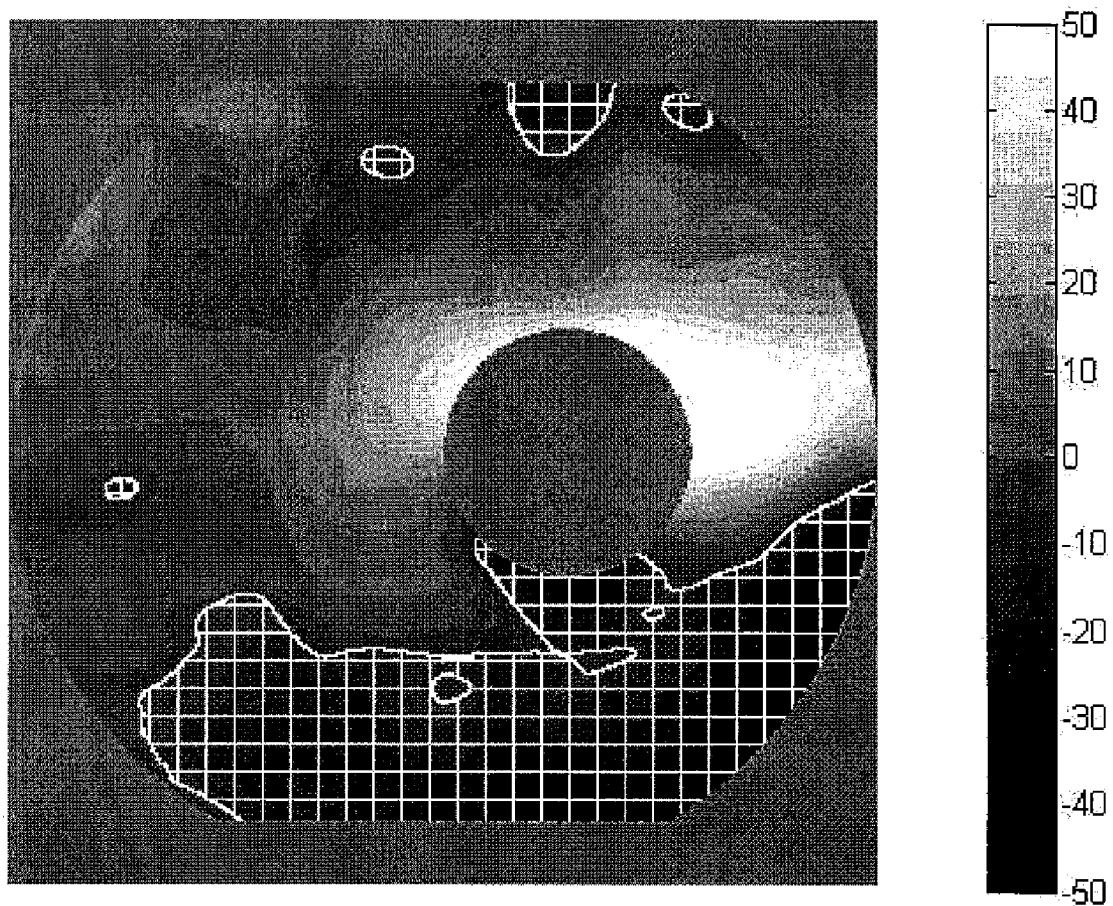
FIG. 7 shows an exemplary GCC PD map of a glaucomatous eye with areas of statistically significant focal thinning marked by the hatch pattern. The unit is %.

Abnormal areas of GCC thinning is identified using the GCC thickness, D or FD map as described in the previous section. Abnormal areas are identified on the PD map (FIG. 7) and the negative values of PD in the abnormal area are summed (area integral) to obtain the pattern deviation focal loss volume (PD_FLV). This procedure is slightly different from the computation of FLV from D or FD maps in that positive values of PD are set to zero (effectively ignored) in the summation procedure. Preferably the PD_FLV is normalized by dividing the map area so it can be expressed as a percentage.

Although the PD-FLV example above is computed from the GCC thickness map, it can also be computed from other types of maps such as reflectance map. The peripapillary NFL map could also be used as a basis for computing the PD-FLV.
Focal Loss Volume (FLV) and Global Loss Volume (GLV)

To combine FD-FLV map and PD-FLV, focal loss volume (FLV) is define as the summation of negative Fraction deviation in the abnormal area identified by pattern deviation. Usually FLV is normalized by dividing the map area so it can be expressed as a percentage.

The FLV is more specific than FD_FLV and PD-FLV because it only sums up areas where the GCC is thinned both in absolute and relative terms.

Global loss volume (GLV) is defined as the summation of negative fraction deviation in the whole area. Usually GLV is normalized by dividing the map area so it can be expressed as a percentage.

GLV had better repeatability than FLV as it requires less criterion in calculation.

Although the FLV and GLV above is computed from the GCC thickness map, it can also be computed from other types of maps such as reflectance map or nerve fiber thickness map. The peripapillary NFL map could also be used as a basis for computing the FLV and GLV.
Other Types of Pattern Analysis for Detecting Abnormality
Average Overall and sectional averages can be computed on the thickness map, deviation map or FD map.

Overall average is averaged from all valid regions of the map.

Superior average is averaged from all valid regions in the superior hemisphere of the map.

Inferior average is averaged from all valid regions in the Inferior hemisphere of the map.
Asymmetry Glaucoma affects the inferior half of the eye more severely in most cases. But in a minority of cases it can also affect the superior half of the eye more severely. Therefore it is preferable to compute the absolute deviation from normal for superior-inferior difference (SID) for the purpose of glaucoma detection.

$$SID = Superior\_average - Inferior\_average$$

The absolute deviation of superior-inferior difference (ADSID) is the absolute value of the difference between SID in the test eye and the average normal eye.

$$AD\_SID = Abs(SID - normal\_mean\_SID).$$

pattern coefficient of variation (Root-mean-square)

Figure 9:
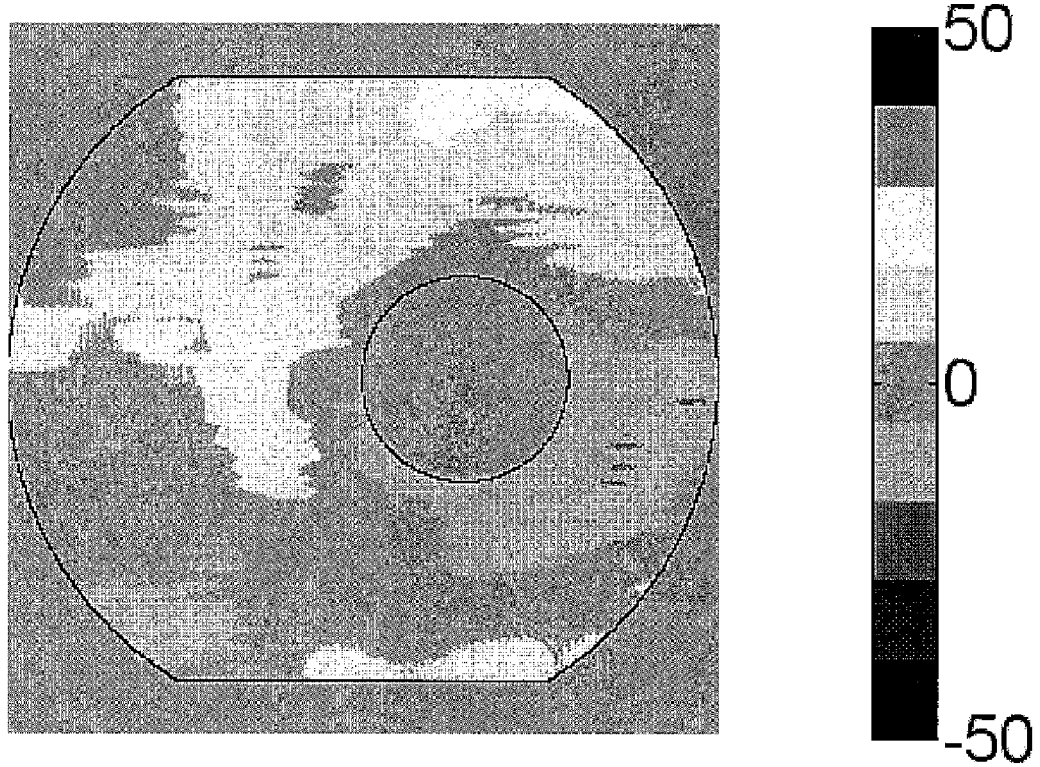
FIG. 9 shows an exemplary deviation map of total retinal thickness in the macula obtained from a glaucomatous eye. The unit is μm.
Figure 10:
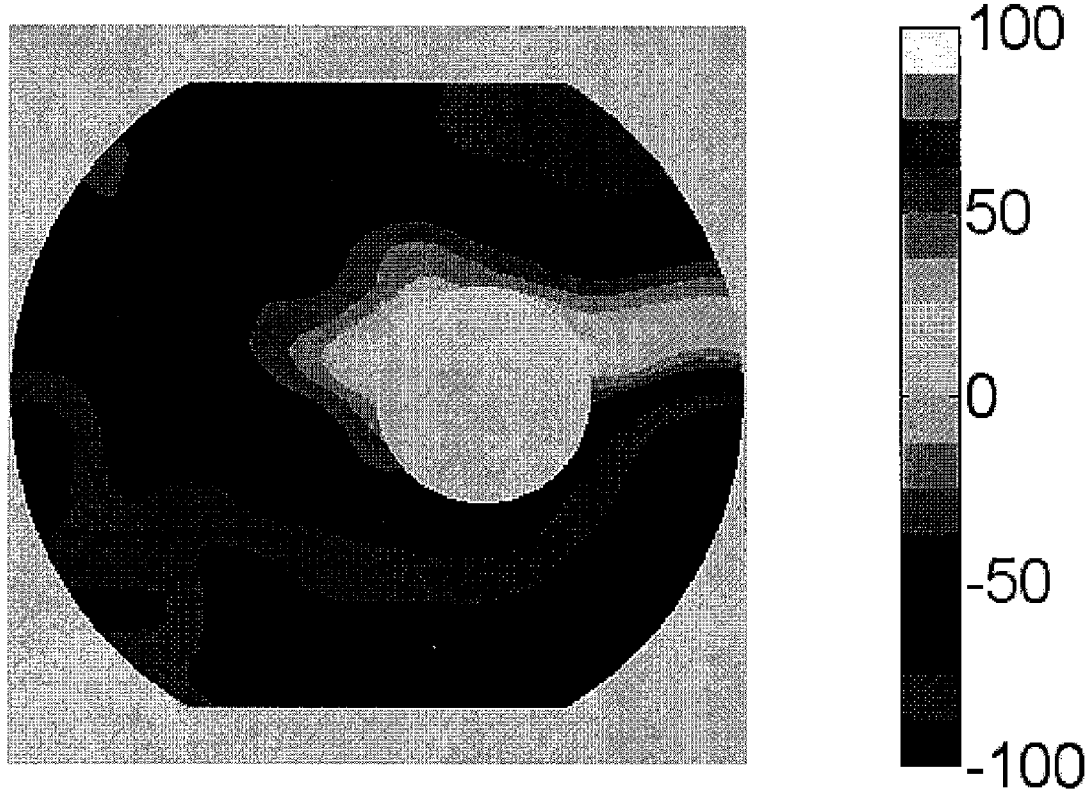
FIG. 10 shows an exemplary fractional deviation map of summed GCC/ORC reflectance ratio obtained from a glaucomatous eye. The unit is %.
Figure 11:
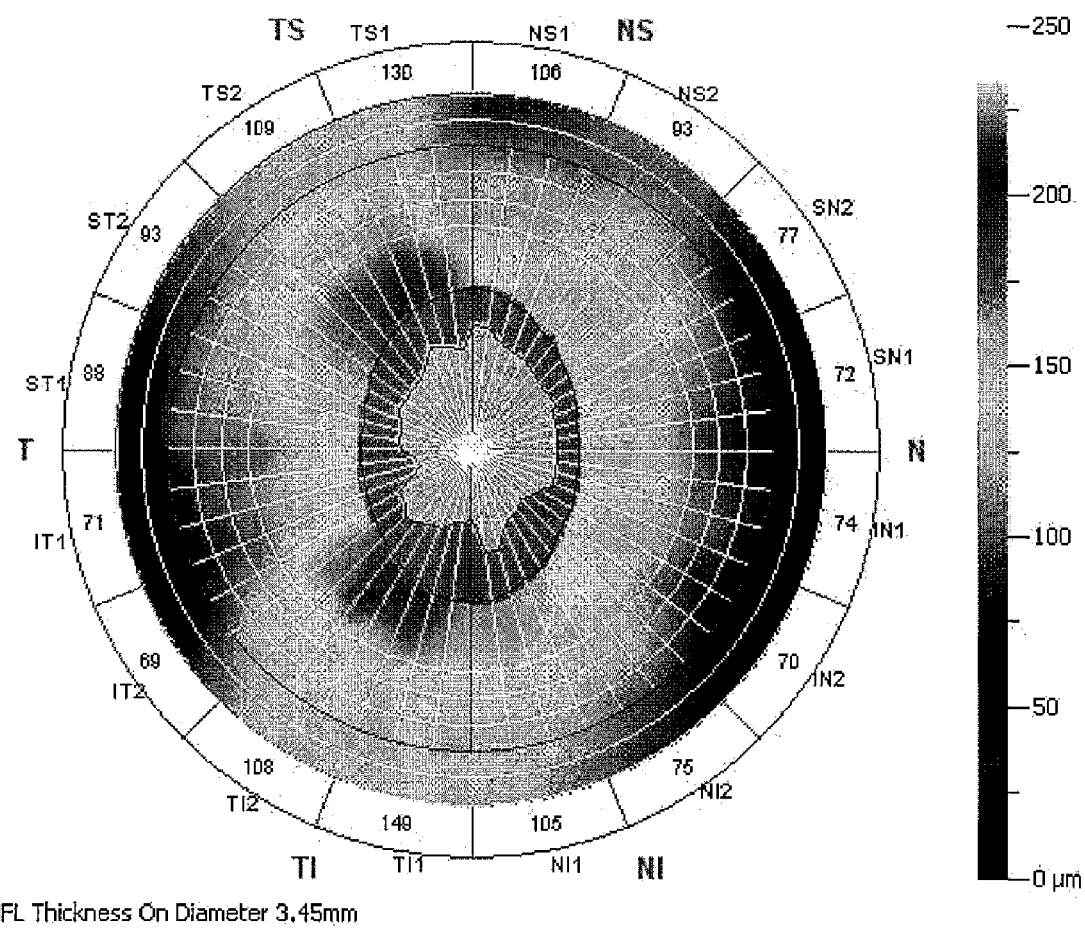
FIG. 11 shows an exemplary normal peripapillary NFL thickness map.
Figure 12A:
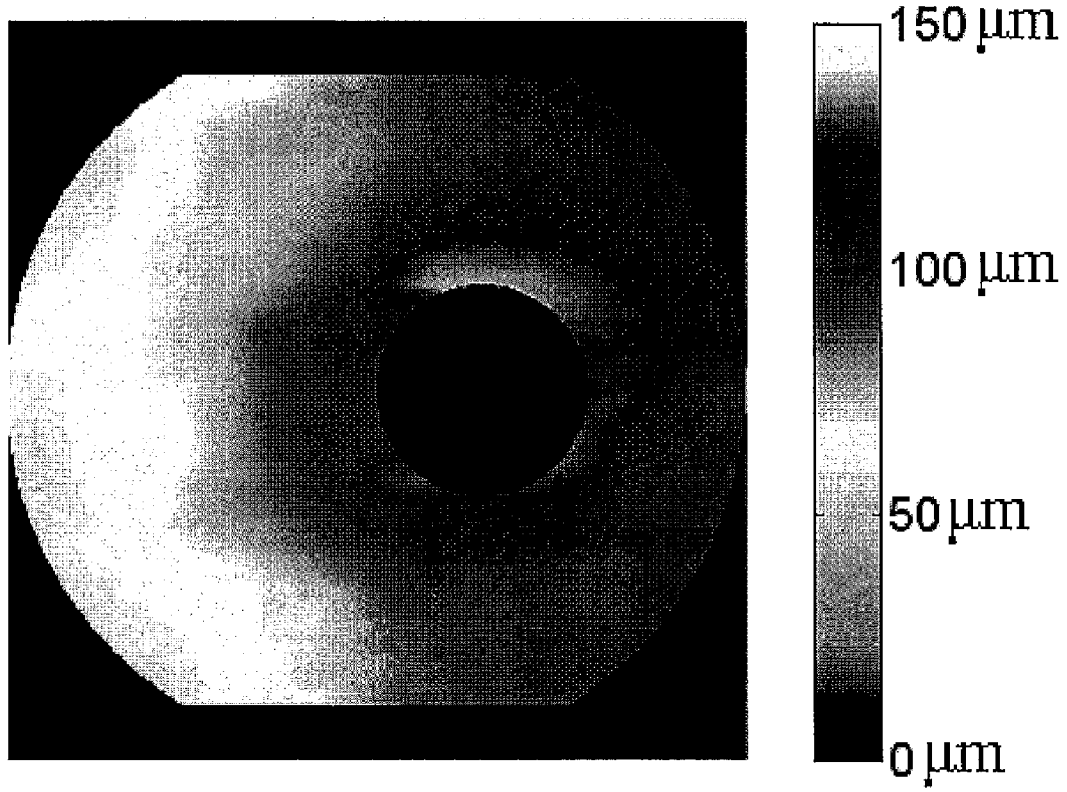
FIG. 12 shows an exemplary set of maps for a perimetric glaucoma case. All of the macular GCC thickness (mGCCT) parameters were abnormal (average=71 μm, $p<0.5\%$; focal loss volume=12.6%, $p<0.5\%$, global loss volume=26.5%, $p<0.5\%$; pattern coefficient of variation=21%, $p<0.5\%$; superior-inferior difference=17.0 μm, p<0.5%). (A) shows an exemplary mCCCT map. (B) shows an exemplary fractional deviation map with areas of significant focal loss marked by the hatching pattern. (C) shows an exemplary pattern deviation map. (D) shows an exemplary disc photo showing inferotemporal rim loss. (E) shows an exemplary visual field (VF) pattern deviation (PD) map. The VF was abnormal (pattern standard deviation=16.5dB, p<0.5%; glaucoma hemifield test was outside normal limits. The elliptical dashed line shows the area corresponding to the mGCCT maps. The superior VF defect corresponded to the inferior ganglion cell loss and disc rim thinning.
Figure 12B:
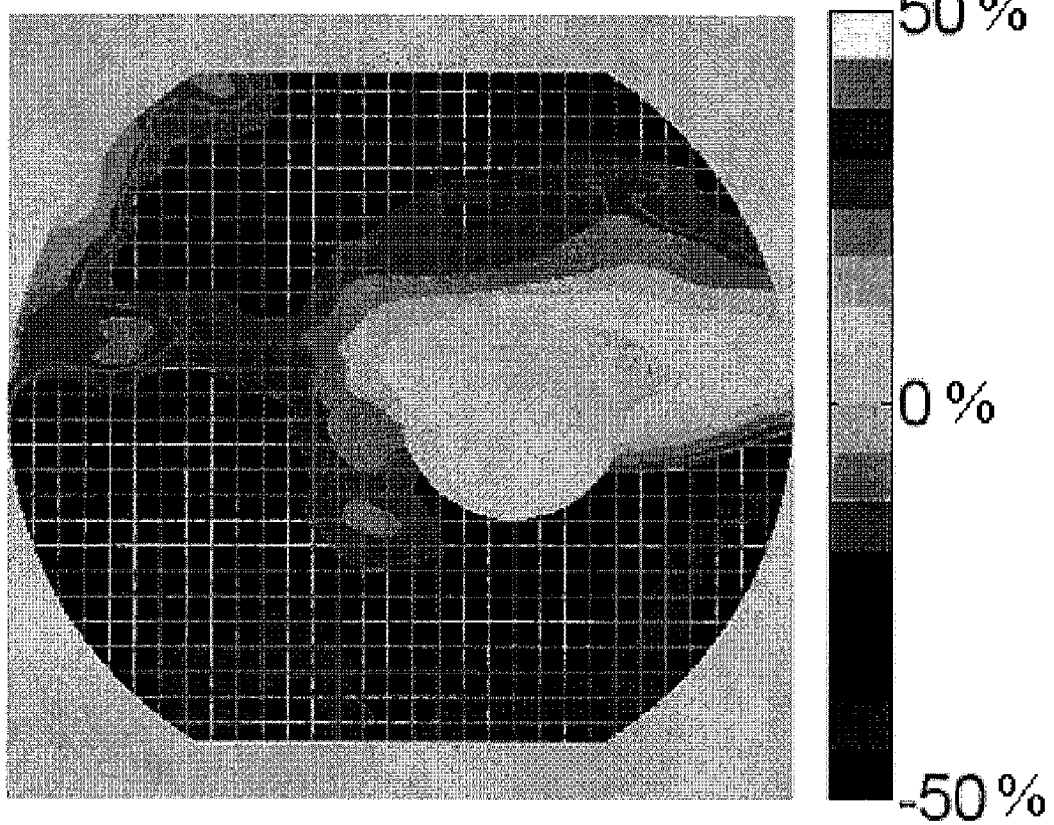
Figure 12C:
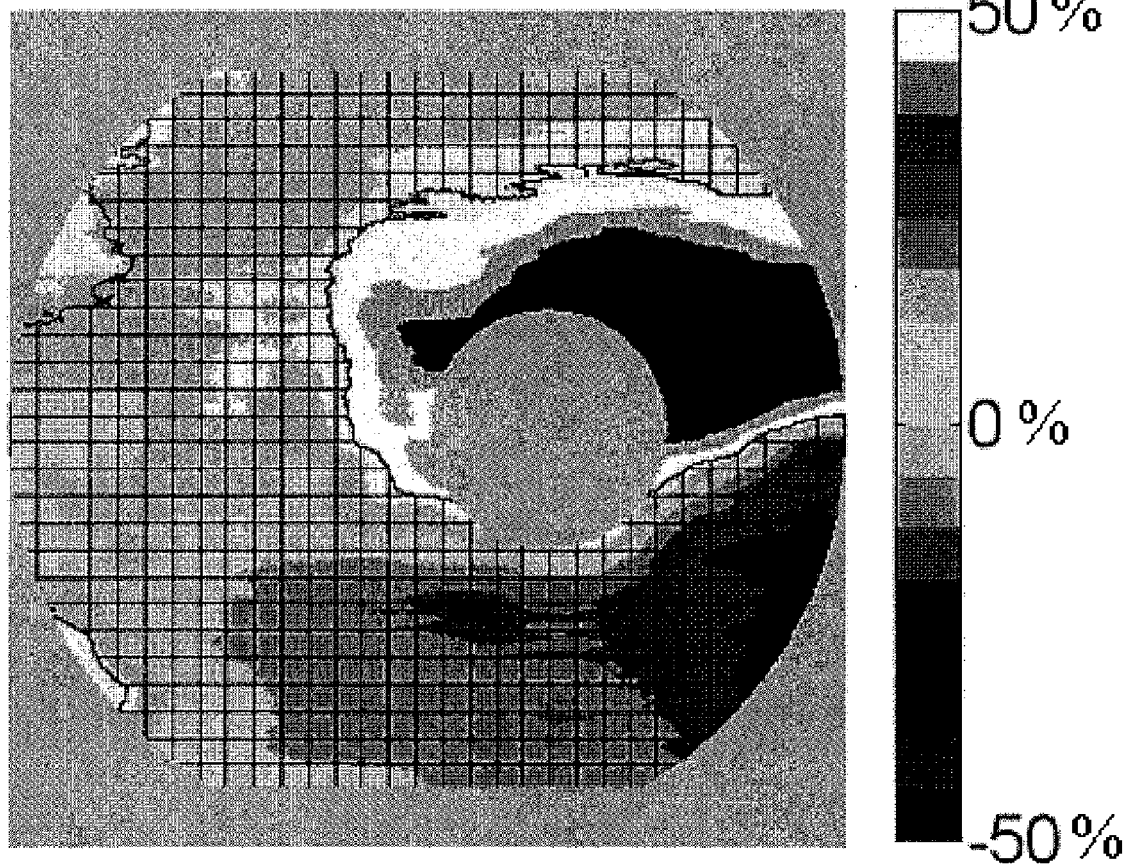
Figure 12D:
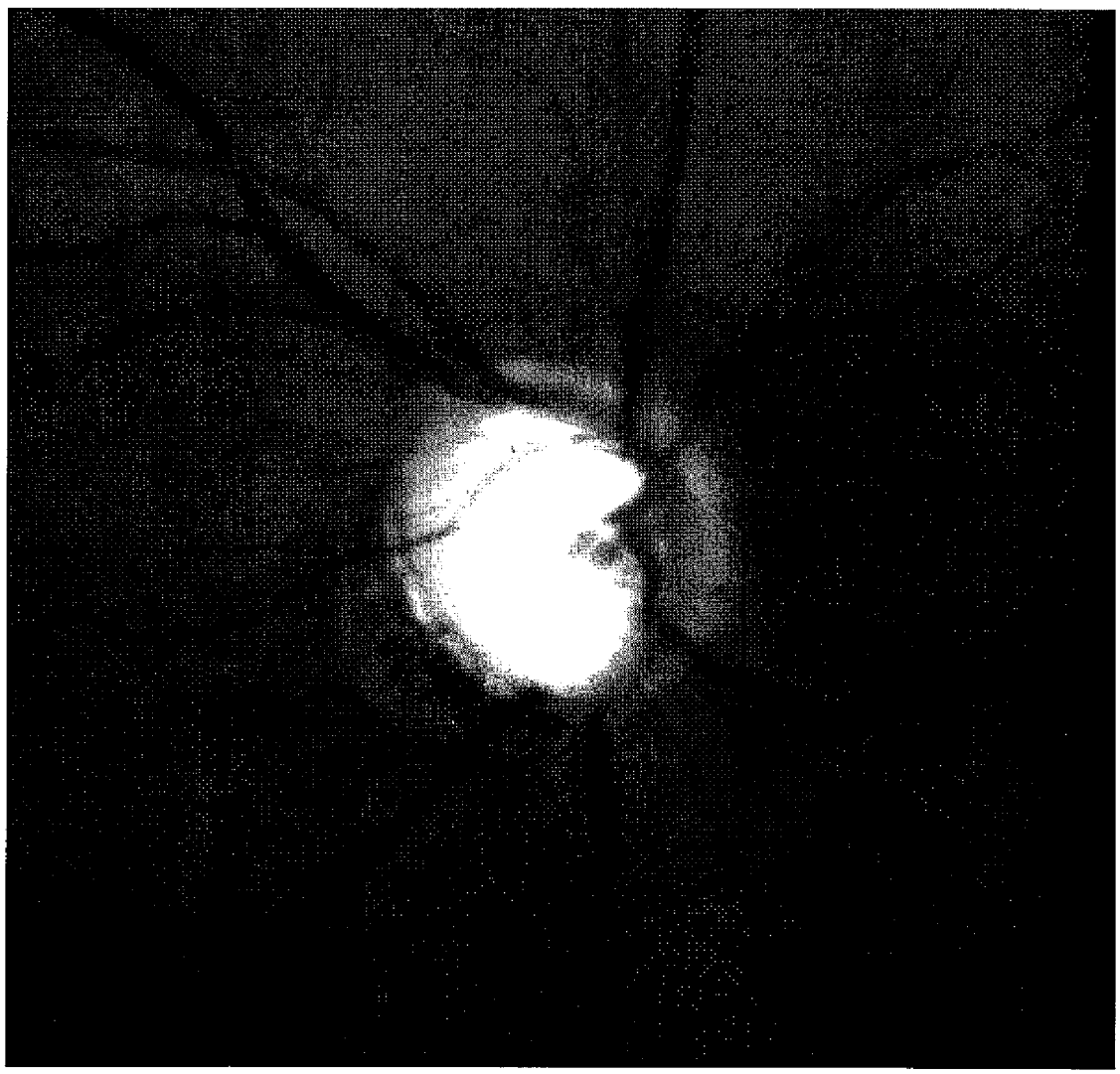

The pattern coefficient of variation (PCV), or root of mean square (RMS), could be computed from deviation map, FD map and PD maps. It is most useful for the PD map and provides a summary of deviation from normal pattern. For example, root-mean-square pattern deviation (RMS-PD) parameter is computed by the following formula:

$$RMS\_PD = (1/A)^* (\int_A PD^2 dx dy)^{1/2}$$

where A is the area of the map, PD is the pattern deviation value on the map, x is the horizontal dimension of the map, and y is the vertical dimension of the map.
Other Types of Maps Retinal maps other than those described above could also be used to compute diagnostic parameters as described above.
Other Thickness Maps Total retinal thickness map (FIG. 9) and thickness maps of NFL, GCL, IPL, INL and all their possible combinations could be used for glaucoma diagnosis by computing pattern parameter according to the present invention. The average thickness of these combinations have been explored in glaucoma diagnosis [1-2].
Reflectance Ratio Maps Glaucoma not only cause thinning of inner retinal layers, but also reduces the amplitude of reflected signal from these layers. Thus maps of inner retinal reflectance are also of interest. Preferably, the variation in reflectance from factors extrinsic to the retina (poor focusing, media opacity) are removed by taking the ratio of the average signal within the inner retinal layer and dividing it by the average signal from a reference layer. The reference layer could be the bright photoreceptor inner segment-, outer segment and their junction (IS-OS), the retinal pigment epithelium (RPE), the choriocapillaris, or some combination of them. The combination of IS-OS and RPE is called the outer retinal complex (ORC). Reflected signals from these layers could be summed or averaged to provide diagnostic information. They are called sum reflectance ratio map (FIG. 10) and average reflectance ratio maps, respectively. The fractional deviation map of the sum reflectance ratio is preferred.
Peripapillary Maps The map of NFL or retinal thickness around the optic nerve head (peripapillary) also provides information for glaucoma diagnosis. Peripapillary NFL reflectance ratio maps can also be used. All of the pattern parameters described in the present invention could be applied. On the RTVue OCT system, the NFL thickness map (FIG. 11) is preferably measured using the Optic Nerve Head 4-mm (ONH4) scan pattern.

4. Diagnosis Determination

In the fourth stage, a diagnosis is determined based on the computed diagnostic parameter. In this stage, comparison to other reference data may be beneficially employed. In one exemplary embodiment, a cross-correlation analysis is performed to differentiate among different types of optic neuropathies.

Pattern Cross-Correlation to Differentiate Between Various Types of Optic Neuropathy Different types of optic nerve disease causes different patterns of GCC thinning. Glaucoma relatively spares the centrocecal area and has variable superior or inferior dominance (usually inferior). Anterior ischemic optic neuropathy (AION) usually affects either the superior (most) or the inferior half of the macula. Optic neuritis is often connected with multiple sclerosis (MS). It produces a diffuse loss. Pattern matching using cross-correlation is preferably used to distinguish between these types of optic neuropathy.

Figure 8:
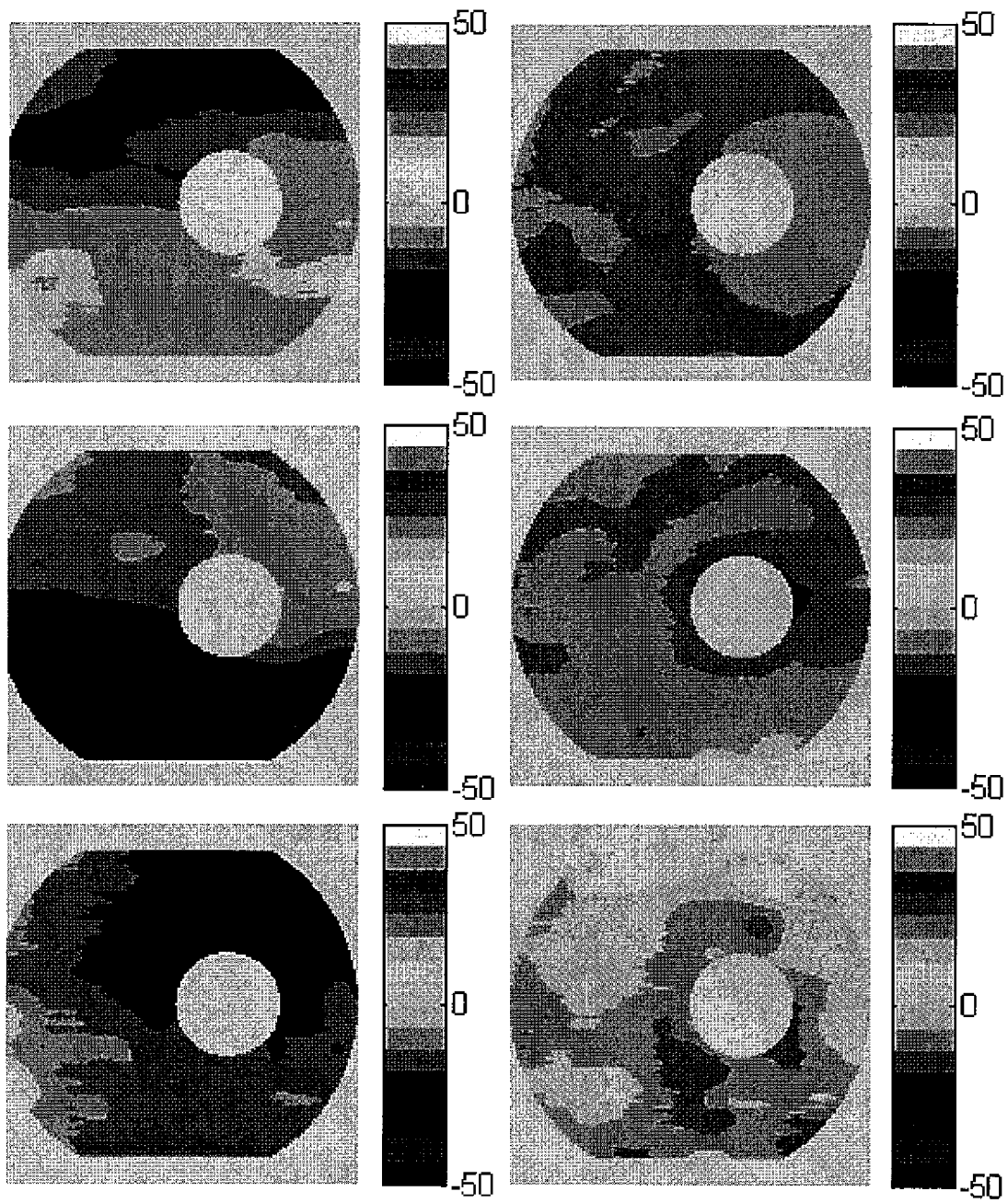
FIG. 8 shows a set of exemplary characteristic PD maps for various optic neuropathies. Upper left: inferior glaucoma (IG), 35 eyes, Upper right: even glaucoma (EG), 41 eyes. Mid left: superior glaucoma (SG), 18 eyes, Mid right: optic neuritis (ON), 22 eyes. Lower left: superior AION (SAION), 11 eyes. Lower right: Inferior AION (IANON), 7 eyes. The units are %.

The analysis could be performed using D, FD or PD maps. Preferably the PD map is used. The characteristic maps for the following types of optic neuropathies (FIG. 8) have been compiled by averaging the maps of eyes within each disease category.

1. Inferior glaucoma (IG): average map of perimetric glaucoma eye with SID value>mean+1 SD of normal.
2. Even glaucoma (EG): average map of perimetric glaucoma eye with SID value within±1 SD of normal.
3. Superior glaucoma (SG): average map of perimetric glaucoma eye with SID value<mean−1 SD of normal.
4. Optic neuritis (ON): average map of optic neuritis cases.
5. Superior AION (SA): average map of AION eyes with SID<normal.
6. Inferior AION (IA): average map of AION eyes with SID>normal.

Characteristic maps for other types of optic neuropathy can also be similarly derived. For example toxic, metabolic and nutritional optic neuropathy should produce central or centrocecal GCC loss.

The pattern cross-correlation (PCC) value is computed by cross correlation of the map under testing with the characteristic maps of all of the characterized optic neuropathies. A diagnosis is then chosen based on the highest PCC value. PCC can defined from one of the maps, such as fraction deviation map, pattern deviation map and deviation map. For example, PD-PCC can be defined as:

$$PCC = \int_A (PD * CPD) / \left[ \frac{\left(\int_A PD * PD \, dx \, dy\right)^{1/2}}{\left(\int_A CPD * CPD \, dx \, dy\right)^{1/2}} \right]$$

where A is the area of the map, PD is the pattern deviation of the eye being tested, CPD is the characteristic pattern deviation of the disease under consideration, x is the horizontal dimension of the map, and y is the vertical dimension of the map. Using FD and D map, we can create similar parameter called FD-PCC and D-PCC. For GCC map, we prefer to use fraction deviation map to calculate the PCC for glaucoma analysis. For peripapillary NFL map, we prefer to use deviation map to calculate the PCC for glaucoma analysis.

Comparison of Diagnostic Power

To assess the diagnostic power of GCC-derived parameters, we use the area under receiver-operating characteristic curve (AROC), which summarizes sensitivity and specificity of diagnosis over the total range of applicable diagnostic thresholds. The data was from the AIGS using the subset of normal and perimetric glaucoma subjects who had undergone testing with both RTVue and Stratus testing. Table 1 shows that many GCC-derived parameter are superior to the average retinal thickness. More sophisticated pattern analysis is superior to simple averaging. Best performance was obtained with PD_FLV. Nearly equivalent diagnostic power was also obtained from FLV maps computed from either deviation or fractional deviation maps.

The following specific example is provided to further illustrate the present invention.

EXAMPLE

Detection of Macular Ganglion Cell Loss in Glaucoma

Methods
1. Clinical Study

Participants in the prospective Advanced Imaging for Glaucoma Study (AIGS) between the periods of 2003 and 2007 were included. These participants were classified into four groups: normal (N), perimetric glaucoma (PG), glaucoma suspect (GS) and pre-perimetric glaucoma (PPG). Only the data from the baseline visit was used. The GS group was not used in this study because the members' glaucoma status was indeterminate. We used only data from AIGS centers that employed FD-OCT during the study period. The eligibility criteria for the three groups analyzed are briefly described below.

The N group participants had intraocular pressure (IOP) of less than 21 mm Hg for both eyes, a normal Humphrey SITA 24-2 visual field (VF) [mean deviation (M) and pattern standard deviation (PSD) within 95% limits of the normal reference and a glaucoma hemifield test (GHT) within 97% limits], a central corneal thickness $\geqq 500 \, \mu m$, a normal-appearing optic nerve head, a normal nerve fiber layer, an open anterior chamber angle, and no history of chronic ocular or systemic corticosteroid use.

The PG group participants had at least one eye that fulfilled the following criteria: glaucomatous (abnormal) VF loss [PSD (P<0.05) or GHT (P<1%) outside normal limits in a consistent pattern on both qualifying VF's] and optic nerve head (ONH) changes such as diffuse or localized rim thinning, disc (splinter) hemorrhage, vertical cup/disc ratio greater than the fellow eye by >0.2, notch in the rim, or previous photographic documentation of progressive excavation of the disc, progressive thinning of the neuroretinal rim or NFL defects visible on slit-lamp biomicroscopy, or progressive loss of NFL.

The PPG group participants had same criteria for ONH change as defined for the PG group. But the VF of the PPG participants' eyes did not meet the eligibility criteria for the PG group.

Exclusion criteria for all groups in the AIGS are: best-corrected visual acuity worse than 20/40; age <40 or >79 years; spherical equivalent refractive error >+3.00 D or <−7.00 D; diabetic retinopathy or other diseases that could cause visual field loss or optic disc abnormalities; or previous intraocular surgery other than an uncomplicated cataract extraction with posterior chamber IOL implantation.

The research was conducted in accordance with the Declaration of Helsinki. Informed consent was obtained from all participants after the goals of the study and consequences of participation had been discussed. The institutional review board of each institution involved in the study approved the research protocol. Further description of the AIG Study protocol can be found in the AIGS Manual of Procedure (the manual is available for download from the AIG Study website, the content of which is incorporated herein by reference).

2. Fourier-Domain Optical Coherence Tomography

Patients were scanned using the RTVue FD-OCT system (Optovue, Inc. Fremont, Calif.), which acquires 26,000 axial scans (a-scans) per second and has a 5-µm depth resolution (full-width half-maximum). In comparison, the standard Stratus TD-OCT system (Carl Zeiss Meditec, Dublin, Calif.) acquires 400 a-scans per second and has a 10-µm resolution. Taking advantage of the higher speed of the FD-OCT, we devised three-dimensional scans of the macular region called a macular map 7 mm scan (MM7) that evenly samples the macula over a 7 mm square area (FIG. 1). The center of the MM7 protocol is shifted 0.75 mm temporally to improve sampling of the temporal periphery. The MM7 pattern consists of 14928 a-scans from one horizontal line and 15 vertical lines with 0.5 mm intervals. The scan time for the MM7 pattern is 0.6 second. Three MM7 scans were acquired on the baseline visit of each AIGS participant. The raw data were exported for further image processing.

3. Image Processing

We developed automated software to map mGCCT. First, the 15 vertical OCT cross-section images (see FIG. 2 for an exemplary cross-sectional image) were aligned to the horizontal image by cross correlation to build a registered three-dimensional (3D) image set. The images were smoothed with a combination of median filter and Gaussian filter to a lower resolution to suppress background and speckle noises. They were then re-sampled at lower definition to speed computation. The subsequent steps used images at various resolutions and definitions chosen to optimize the robustness and speed of processing. The photoreceptor pigment epithelium complex (PPC) band, which includes the bright bands of the photoreceptor inner segment-outer segment (IS/OS) junction and the retinal pigment epithelium, was detected as the second (counting from the inner side) maximum peak in a low-resolution image. The IS/OS junction was then detected as the first maximum intensity peak within the PPC. Small portions of the PPC had low signal due to shadowing from overlying blood vessels; these shadowed a-scans were replaced by adjacent a-scans to avoid interruption of boundary detection. The images were aligned at the IS/OS junction to facilitate lateral smoothing. The inner limiting membrane (ILM) was identified as the first positive gradient peak of each a-scan. Neighbor constraint and a knowledge model were used to distinguish the ILM peak from spurious noise or detached vitreous face. The outer boundary of the inner plexiform layer (IPL) was then identified. To improve the robustness of boundary detection, a progressive refinement procedure was applied. The procedure starts with boundary detection on a low-resolution (highly low-pass filtered) 3D data set and then progressively refines the boundary on progressively higher resolution data. The GCC thickness was measured from the ILM to the outer IPL boundary. Retinal thickness was measured from the ILM to the IS/OS junction. The mGCCT and mRT maps were computed by interpolation of the thickness profiles from the 16 OCT cross-sectional images in the MM7 3D dataset. The position of the foveal depression was identified on the mRT map and used to recenter the vertical position of the maps. The maps were cropped to remove peripheral areas where segmentation was less reliable. The remaining areas are those within a 7 mm diameter circle and within 3 mm from the central horizontal line. For the mGCCT map, the area within 0.5 mm of the foveal center (1 mm diameter circle) was also excluded because the GCC is too thin to be reliably measured.

4. Derivation of Diagnostic Parameters

FIG. 12 shows a set of maps for the perimetric glaucoma (PG) case. We computed several glaucoma diagnostic parameters based on the mGCCT map (FIG. 12A). The simplest was the overall average thickness (mGCCT-AVG). As glaucoma tends to produce more inferior damage, we also computed the difference between superior and inferior hemispheric averages (mGCCT-SID).

To extract even more diagnostic information from the mGCCT map, we developed methods of analyzing the pattern of mGCCT loss. To do this, we computed maps of mGCCT loss: the fractional deviation (FD) map and the pattern deviation (PD) map. First the GCC maps of all normal eyes were averaged, point by point, to create a normal reference map. The FD map (FIG. 12B) is the mGCCT map under consideration minus the normal reference map divided by the normal reference map. The pattern map is the GCC thickness map normalized (divided) by its own overall average. The pattern deviation (PD) map (FIG. 12C) is the pattern map under consideration minus the normal reference pattern. The FD map shows the percentage of GCC loss. The PD map shows how the mGCCT pattern differs from normal.

Three pattern-based diagnostic parameters were then computed from the two derivative maps. The focal loss volume (FLV) is the sum FD in the region where there is significant focal loss. Significant focal loss is defined as FD more than 1.65 standard deviations (SD) below the normal average (below the fifth percentile of normal distribution). Global loss volume (GLV) is the sum of FD in areas where FD is negative. Pattern coefficient of variation (PCV) is the root mean square of the PD map.

The image processing and diagnostic parameter calculations were programmed in MATLAB 7.0.

5. Time-Domain Optical Coherence Tomography

All participants were also scanned by Stratus OCT (Carl Zeiss Meditec, Inc, Dublin, Calif.), using the standard fast retinal nerve fiber layer (RNFL) scan and the fast macular thickness map scan. The overall averages of cpNFLT and mRT were calculated using the standard Stratus 4.0 software.

6. Statistical Analysis

Both eyes of each participant were analyzed. The inter-eye correlation was accounted for in statistical tests by the use of a generalized estimating equation (GEE) approach or linear mixed model.

Intraclass correlation, pooled SD, and coefficient of variation (CV) were used to evaluate the reproducibility of diagnostic parameters. These indices were computed from linear mixed models in which the variance components for subject and eye were used to account for repeated measurements and inter-eye correlation, respectively.

Area under the receiver operating characteristic (AROC) curve was used to compare diagnostic power. To account for inter-eye correlation, the AROC was computed based on the formula of Obuchowski, which extended the nonparametric method of Delong et al. as applied to clustered data. The same method has been used in previous studies in ophthalmology to handle inter-eye correlation.

To adjust for age imbalance between the N, PG and PPG groups, a GEE logistic regression model with age and diagnostic parameter in covariates was used to generate the AROC. This method of compensating for age imbalance has been used in a previous ophthalmology study.

To compare the means, we used the t-test for parameters that followed a normal distribution. Several diagnostic parameters were found to follow the Gamma probability distribution (a non-normal distribution). The means of these parameters were compared using the Wald test with generalized linear models for the appropriate Gamma distribution. A GEE adjustment for inter-eye correlation was used for the tests. The tests were performed in a one-tailed manner since we hypothesize that the means in the diseased groups are lower than in the normal group.

The AROC calculations were written in MATLAB 7.0 software and the other statistical calculations were performed with the SAS 9.1 software. The critical alpha level of statistical significance was set at 0.05.

Results

A total of 180 participants (328 eyes) with available RTVue FD-OCT MM7 scans and valid Stratus TD-OCT scans were identified from the AIG central database. Fifteen eyes of 14 participants were excluded because of visibly inaccurate segmentation for all three repeated MM7 scans. The remaining 313 eligible eyes from 179 participants were analyzed. The demographic and clinical information for each group is summarized in Table 1. Pre-perimetric glaucoma and PG participants were older than N participants (P<0.0001). The age imbalance was appropriately handled in subsequent analyses as stated in the methods section. There were more Caucasians in the N group compared to PG group. However, there was no significant difference between the racial groups in terms of the means of diagnostic parameters in the N group. As expected and classification of eye status, N eyes performed better in VF tests than PPG and PG eyes in terms of MD and PSD measurements. N eyes had lower IOP and thicker central corneal thickness (CCT) than PPG and PG eyes. The difference is significant in IOP of the PPG eyes and in CCT of the PG eyes.

To classify the PG eyes in different stage of glaucoma based on MD, 79 eyes (70.5%) had early glaucoma (MD≧−6.0 dB), 25 eyes (22.3%) had moderate glaucoma (MD between −6.01 to −12.0 dB), and 8 eyes (7.1%) had advanced glaucoma (MD<−12 dB).

Table 2 summarizes the distribution statistics of each diagnostic parameter by group. All parameters were significantly worse in the PPG and PG groups compared to the N group (P<0.001). Because SID, PCV, FLV and GLV had nonnormal distributions (Gamma distributions), these parameters were compared using the Wald test as described in the methods section.

Figure 13:
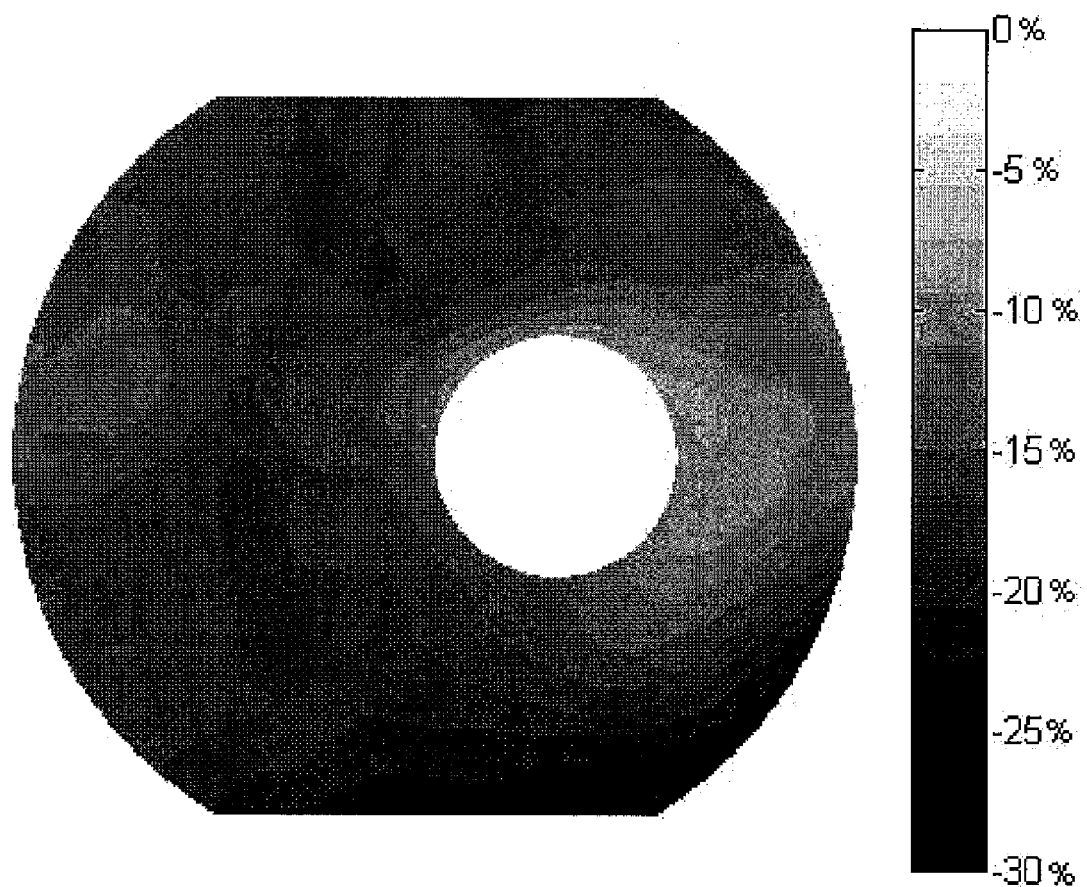
FIG. 13 shows an exemplary image of the average mGCCT fractional deviation map of PG eyes. This represents the characteristic pattern of ganglion cell loss in glaucoma.

The characteristic pattern of mGCCT loss in glaucoma is bi-arcuate, with greater inferior defect (FIG. 13).

Repeatability was assessed by three measures: ICC, pooled SD, and CV of repeated measures (Table 3) taken in the same session. The repeatability in the PPG and PG groups is important because it provides an indication of how well a parameter can track progression through stages of the disease. Overall, FD-OCT mGCCT and mRT averages and GLV had excellent repeatability (ICC=0.99 and CV<1.3% in the PG and PPG groups). Although the TD-OCT mRT and cpNFLT averages also had good repeatability, they were not as good as comparable FD-OCT parameters.

The AROC provides a measurement of diagnostic power (Table 3). The mRT average measured by FD-OCT and TD-OCT has equivalent AROC. By isolating the inner retina, mGCCT-AVG improved the diagnosis of PG (AROC=0.90). This is significantly better than for the mRT (P=0.01). The FLV and GLV pattern-based parameters performed even better in diagnosing PG. The increase was significant (P=0.01) for GLV. The macular parameters mGCCT-AVG, mGCCT-FLV, mGCCT-GLV had comparable diagnostic power to cpNFLT-AVG. For the diagnosis of PPG (versus N), we found no advantage for mGCCT parameters over mRT.

The odds ratio (95% confidence interval) of having glaucoma for every 10 μm loss of tissue was 7.43 (4.13, 13.36) for mGCCT-AVG, 4.88 (2.64, 9.03) for cpNFL and 2.68 (1.96, 3.65) and 2.48 (1.83, 3.35) for FD-OCT and TD-OCT mRT, respectively. We note that for each 10-μm loss of tissue, loss of GCCT-AVG has approximately 1.5 times odds to have glaucoma than the loss of cpNFL-AVG.

Correlation of mGCCT findings with disc photography and VF are shown in example cases of PG and PPG. In both cases, the mGCCT FD map showed a typical bi-arcuate pattern of loss. In the PG case, the predominantly inferior GCC loss correlated well with the inferior disc rim loss and superior VF defect. In the PPG case, the GCC loss was focal, and the abnormality was picked up by the pattern-based parameters but not the average.

Conclusion

In this Example, we showed the application of novel diagnostic parameters in accordance with the present invention to look for glaucoma in the macula. The faster speed of FD-OCT (65× Stratus TD-OCT) allows high density scanning over a large region of the macula with less motion artifact. The resolution of the RTVue FD-OCT device is also two times better than conventional time-domain OCT (e.g., Stratus TD-OCT). The combination of higher definition (denser sampling) and higher resolution improved the precision and robustness of mGCCT measurement.

We also discovered in this Example that the mGCCT average measured by the RTVue FD-OCT were significantly better at diagnosing glaucoma in the PG group, compared to the mRT average measured by either FD-OCT or TD-OCT. Thus, isolating the GCC from the outer retina improved diagnostic power. While not intending to be limited by any particular theory or explanation, we believe that this could be explained by the fact that the outer retina, which is not much affected by glaucoma, takes up 65% to 70% of total retinal thickness and, therefore, could contribute variation in thickness that decreases discriminant power. The diagnostic power of mGCCT was also higher than that of mRT in the discrimination between PPG and N eyes, but the advantage was not statistically significant. This could be explained by the small PPG group size, and the possibility that some eyes in the PPG group may not actually have glaucoma (PPG eyes had normal or borderline VF).

Furthermore, the mRT by either FD-OCT or Stratus TD-OCT was a less sensitive parameter for glaucoma detection (with lower AROCs) than Stratus cpNFL thickness. Other investigators, including Wollestein et al. [4] and Guedes et al. [5] have also reported higher AROCs for Stratus cpNFL thickness compared with Stratus mRT for glaucoma detection. In the current study, the FD-OCT did not offer any significant advantage over TD-OCT for measurement of total macular thickness. Unlike boundary detection for GCC which requires higher resolution and detail provided by FD-OCT due to the necessity for retinal layer segmentation, the boundary detection for mRT can be performed well by lower resolution Stratus TD-OCT since the boundaries of ILM and IS/OS junction are well defined.

Figure 14A:
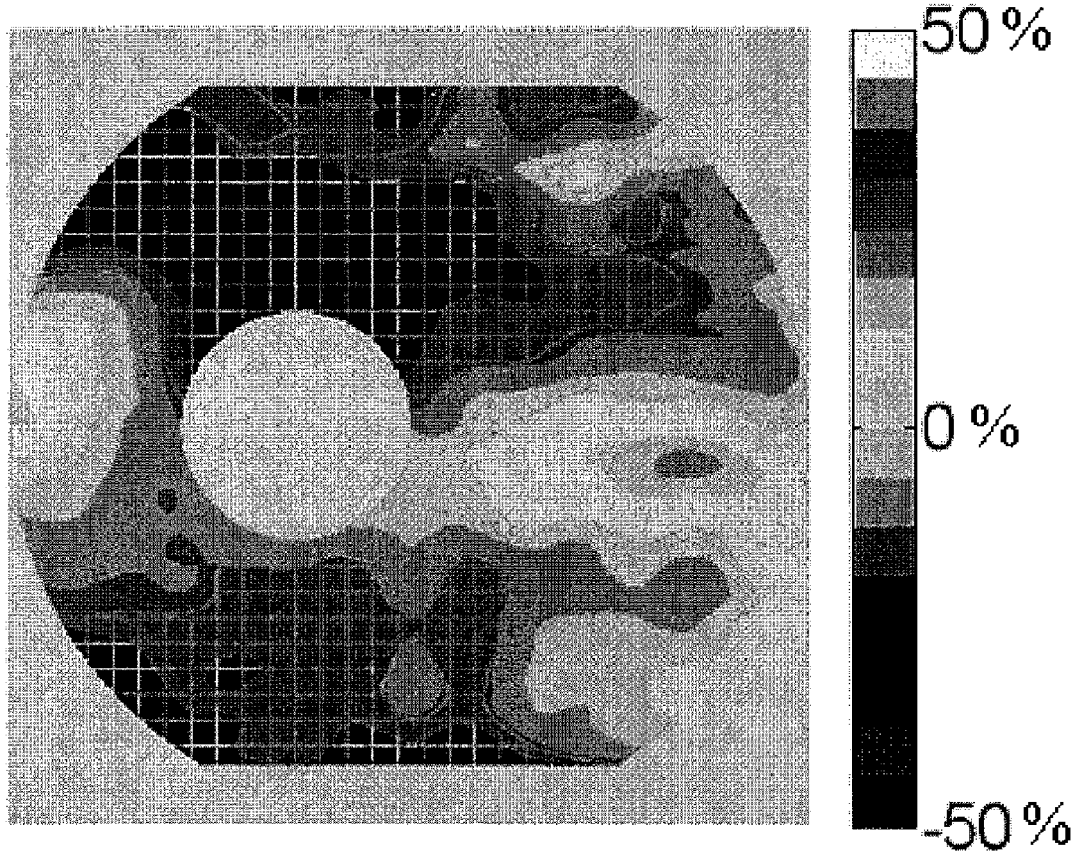
FIG. 14 shows images from an exemplary PPG case example. (A) mGCCT FD map. Some of the mGCCT parameters were abnormal (AVG=82.5 μm, p>5%; FLV=4.9%, P<0.5%, GLV=13.2%, p<0.5%; PCV=0.13, P>5%; SID=−12.1 μm, p<0.5%;) (B) Disc photograph showing early mild thinning of the superotemporal rim. (C) VF PD map.
Figure 14B:
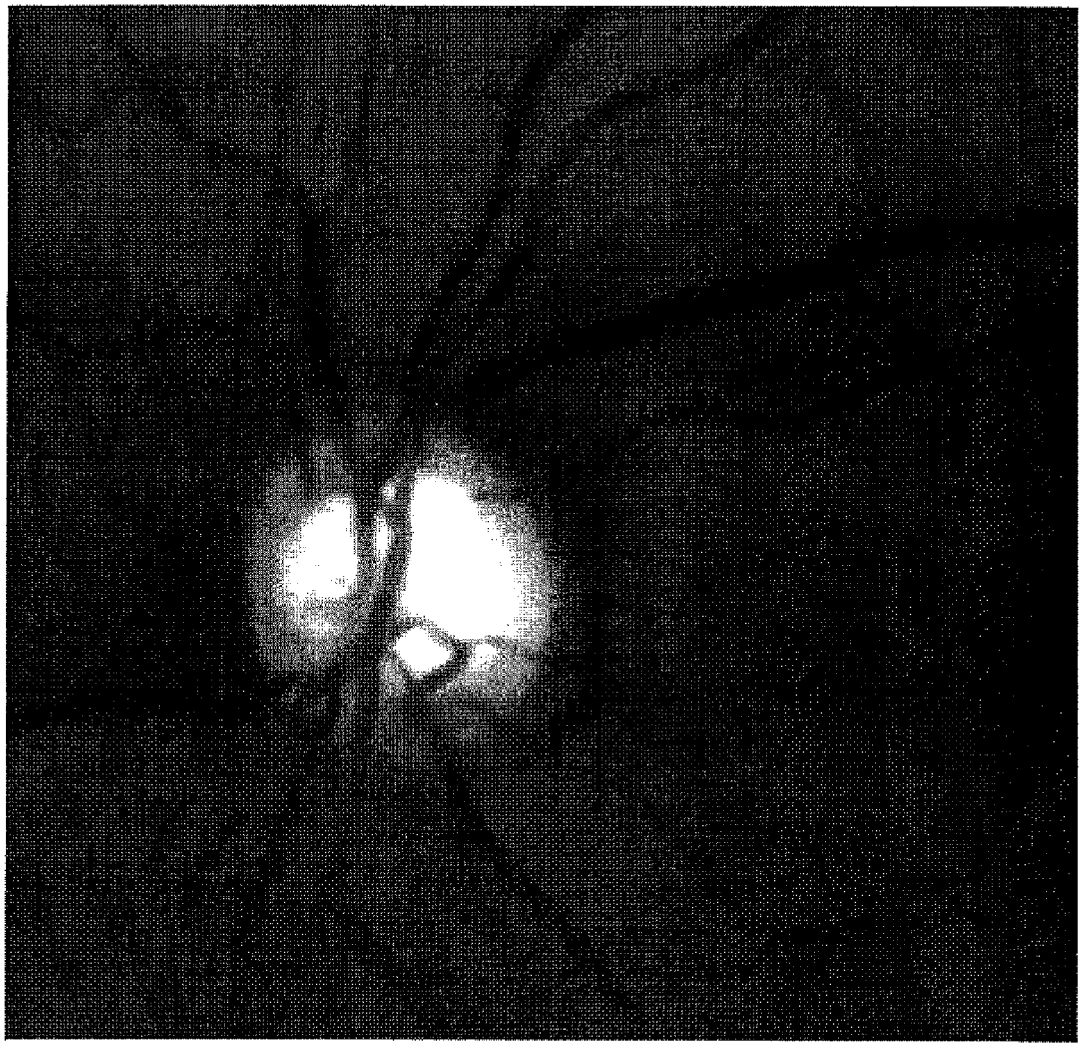
Figure 14C:
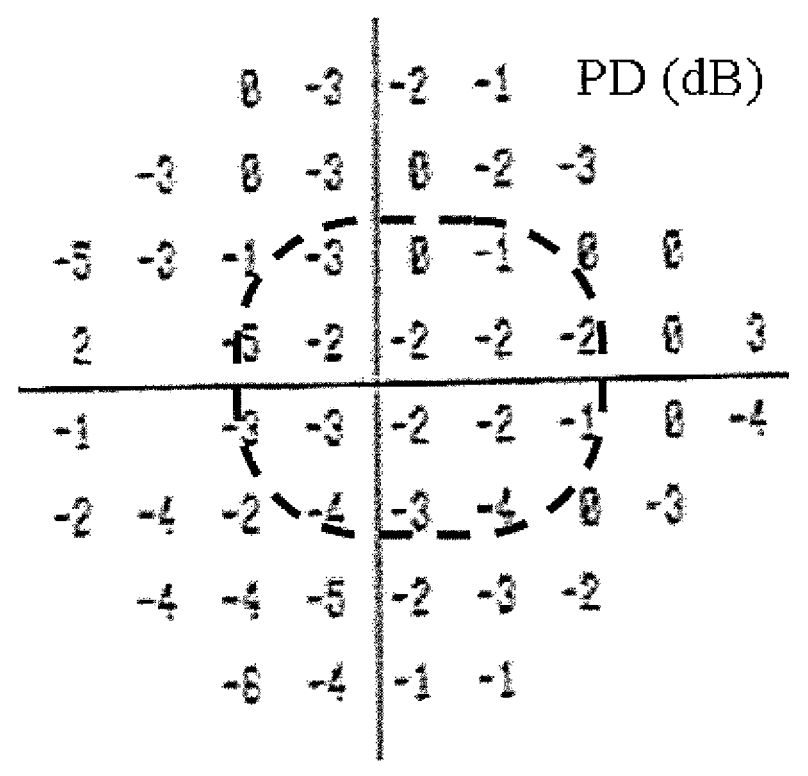

Wider and finer sampling of the macular regions was made possible by the higher speed of FD-OCT. This facilitated the analysis of patterns of GCC loss. We designed several pattern-based parameters that looked at different aspects of the GCC loss pattern and may be used in a complementary fashion. The SID parameter was designed to detect cases where GCC loss is asymmetric, based on the observation that glaucoma often has an inferior-dominant asymmetry. The GLV and FLV parameters sum up the volume of GCC loss in the macula with differing levels of specificity. The FLV parameter is more specific because it only sums loss in regions where the GCC is thin in both absolute (GCCT<normal) and relative (PD<5 percentile) terms. The PCV parameter is purely based on the PD map and detects any change in the GCCT pattern. We found that FLV and GLV had higher diagnostic power than the simple average for the diagnosis of PG. This could be explained by the inclusion of some cases in which the eye may have started with an above average GCCT overall; therefore, looking at the overall average could only detect glaucoma at a later stage. In these cases, looking for abnormality in the GCCT pattern could detect glaucoma earlier. Such a case was presented in FIG. 14, in which the mGCCT average was normal, but the pattern-based parameters were abnormal. This eye probably had thicker than average GCC before it developed glaucoma, as the GCCT along the maculapapular bundle was still above average (FIG. 14). This eye had focal areas wherein the mGGCT was 30% thinner than normal, which was sufficient to be identified as abnormal focal loss by our software. This area corresponded to an area on the VF in which the PD was between −3 and −4 dB, still within the normal range of variation. This case illustrates the utility of mGCCT pattern analysis as an early detection method for diagnosing glaucoma before the patient develops definite VF defects. It also shows that the mGCCT pattern might be a useful correlate in cases where the VF defects are borderline. The reader should be aware that each millimeter on the retina corresponds to about 3.5° on the VF. Therefore the MM7 mGCCT map (7 mm×6 mm) subtends about 11° superiorly and inferiorly, 10° nasally, and 15° temporally. It covers about half of the area of the standard Humphrey 24-2 VF (FIGS. 12E & 14C), and, of course, is up/down reversed relative to the VF due to optical projection in the eye.

In summary, we have demonstrated a wide macular scanning pattern in accordance with embodiments of the present invention which utilizes the higher speed and resolution of FD-OCT. We have also developed GCC mapping software, and new pattern-based diagnostic parameters. The novel mGCCT parameters were able to differentiate glaucoma from nonglaucoma with higher sensitivity and specificity compared to parameters derived from total retinal thickness. On their own, the diagnostic powers of mGCCT parameters were similar to cpNFL parameters and may be used in a complementary fashion. The mGCCT map can be directly correlated with the central portion of the VF map. Some mGCCT parameters were highly reproducible, thus, are useful in tracking glaucoma progression.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

REFERENCES

The following references are each incorporated herein by reference

1. Tan O, Li G, Lu A., et at Mapping of Macular Substructures with Optical Coherence Tomography for Glaucoma Diagnosis, Ophthalmology 2008;115(6):949-56
2. Ishikawa H, Stein D, Wollstein G, et al., Macular segmentation with optical coherence tomography. Invest Ophthalmol Vis Sci 2005;46:2012-7.
3. URL=http:/www.aigstudy.net/
4. Wollstein G, Schuman J S, Price L L, et at., Optical coherence tomography (OCT) macular and peripapillary retinal nerve fiber layer measurements and automated visual fields. Am J Ophthalmol 2004;138(2):218-25.
5. Guedes V, Schuman J S, Hertzmark E, et al., Optical coherence tomography measurement of macular and nerve fiber layer thickness in normal and glaucomatous human eyes. Ophthalmology 2003;1 10(1):177-89.
6. Zeimer R, Asrani S, Zou S, et al. Quantitative detection of glaucomatous damage at the posterior pole by retinal thickness mapping. A pilot study. Ophthalmology 1998; 105(2):224-31.
7. Watanabe Y, Sato M. Quasi-single shot axial-lateral parallel time domain optical coherence tomography with Hilbert transformation. Opt Express 2008;16(2):524-34.

TABLE 1

Characteristics of the Study Populations

| Parameter | Group | | | | |
|---|---|---|---|---|---|
| | Normal (N) | Preperimetric Glaucoma (PPG) | P* | Perimetric Glaucoma (PG) | P** |
| # of Participants*** | 65 | 52 | — | 79 | — |
| # of Eyes | 125 | 76 | — | 112 | — |
| Age (year)**** | 52.9 ± 8.9 | 60.4 ± 9.7 | <0.0001 | 60.5 ± 8.4 | <0.0001 |
| Female (% total) | 68% | 56% | 0.2 | 57% | 0.2 |
| Race % Caucasian | 88% | 79% | 0.2 | 73% | 0.03 |
| MD (dB)**** | −0.1 ± 1.0 | −0.5 ± 1.4 | 0.01 | −4.6 ± 4.3 | <0.0001 |
| PSD (dB)**** | 1.5 ± 0.2 | 1.9 ± 1.0 | 0.001 | 5.9 ± 4.3 | <0.0001 |
| IOP (mmHG)**** | 14.7 ± 2.5 | 16.4 ± 3.3 | 0.004 | 15.1 ± 3.5 | 0.3 |
| CCT (μm)**** | 561.3 ± 36.8 | 560.0 ± 32.4 | 0.7 | 542.7 ± 35.9 | 0.007 |

Abbreviations:
MD = visual field mean deviation;
PSD = visual field pattern standard deviation;
IOP = intraocular pressure;
CCT = central corneal thickness.
P* P values for comparing N and PPG groups
P** P values for comparing N and PG group
***Some participants have one eye diagnosed as PPG and the other eye diagnosed as PG.
****Mean ± standard deviation

TABLE 2

The Distribution of Diagnostic Parameters by Group

| Diagnostic Parameter | N | | PPG | | PG | |
|---|---|---|---|---|---|---|
| | Mean (SD) | Range | Mean (SD) | Range | Mean (SD) | Range |
| RTVue | | | | | | |
| mGCCT-AVG (μM) | 94.8 (7.5) | 76.6, 119.8 | 87.0 (9.3) | 68.6, 114.6 | 79.5 (10.3) | 53.6, 99.1 |
| mGCCT-FLV (%) | −0.7 (1.9) | −17.0, 0.0001 | −2.3 (2.7) | −12.5, 0.0001 | −6.3 (4.3) | −14.5, 0.0001 |
| mGCCT-GLV (%) | −4.3 (4.3) | −21.1, 0.001 | −10.2 (7.0) | −26.6, −0.1 | −17.4 (9.7) | −42.1, −1.0 |
| mGCCT-PCV | 0.076 (0.036) | 0.041, 0.360 | 0.090 (0.034) | 0.051, 0.240 | 0.133 (0.046) | 0.051, 0.227 |
| mGCCT-SID (μM) | 3.4 (2.9) | 0.02, 15.8 | 4.2 (4.0) | 0.1, 21.5 | 7.2 (6.0) | 0.1, 24.9 |
| mRT-AVG (μM) | 228.5 (13.2) | 203.1, 261.6 | 218.9 (12.1) | 194.9, 252.3 | 212.4 (12.4) | 180.9, 237.0 |
| Stratus | | | | | | |
| cpNFLT-AVG (μM) | 98.9 (8.3) | 79.5, 131.4 | 87.7 (13.1) | 60.2, 114.4 | 77.3 (14.6) | 43.5, 127.5 |
| mRT-AVG (μM) | 238.3 (13.0) | 208.0, 264.2 | 229.1 (14.5) | 205.3, 269.7 | 221.8 (14.7) | 180.0, 252.5 |

Abbreviations:

SD = Standard deviation;

mGCCT = macular ganglion cell complex thickness;

AVG = average;

SID = superior-inferior difference;

PCV = pattern coefficient of variation;

FLV = focal loss volume;

GLV = global loss volume;

mRT = macular retina thickness;

cpNFLT = circumpapillary nerve fiber layer thickness.

TABLE 3

Repeatability of Diagnostic Parameters

| Diagnostic Parameters | N | | | PPG | | | PG | | |
|---|---|---|---|---|---|---|---|---|---|
| | ICC | SD | CV | ICC | SD | CV | ICC | SD | CV |
| RTVue | | | | | | | | | |
| mGCCT-AVG (μM) | 0.98 | 1.03 | 1.08 | 0.99 | 1.06 | 1.23 | 0.99 | 0.99 | 1.26 |
| mGCCT-FLV (%) | 0.91 | 0.37 | — | 0.96 | 0.59 | — | 0.95 | 1.00 | — |
| mGCCT-GLV (%) | 0.98 | 0.67 | — | 0.99 | 0.90 | — | 0.99 | 1.02 | — |
| mGCCT-PCV | 0.85 | 0.01 | — | 0.92 | 0.01 | — | 0.93 | 0.01 | — |
| mGCCT-SID (μM) | 0.94 | 1.12 | — | 0.95 | 1.24 | — | 0.97 | 1.60 | — |
| mRT-AVG (μM) | 0.99 | 1.19 | 0.52 | 0.99 | 1.06 | 0.49 | 0.99 | 1.37 | 0.66 |
| Stratus | | | | | | | | | |
| cpNFLT-AVG (μM) | 0.96 | 1.69 | 1.71 | 0.99 | 1.52 | 1.74 | 0.98 | 2.27 | 2.93 |
| mRT-AVG (μM) | 0.97 | 2.16 | 0.90 | 0.93 | 3.66 | 1.60 | 0.96 | 3.07 | 1.38 |

Abbreviations:

ICC = intraclass correlation;

CV = coefficient of variation; the abbreviations of diagnostic parameters are the same as Table 2.

TABLE 4

Diagnostic Power of Parameters

| Diagnostic Parameter | AROC (SE) N vs PG | AROC (SE) N vs PPG |
|---|---|---|
| RTVue | | |
| mGCCT-AVG (μM) | 0.90 (0.02) | 0.78 (0.05) |
| mGCCT-FLV (%) | 0.92 (0.02) | 0.73 (0.05) |
| mGCCT-GLV (%) | 0.91 (0.02) | 0.79 (0.04) |
| mGCCT-PCV | 0.90 (0.02) | 0.72 (0.05) |
| mGCCT-SID (μM) | 0.80 (0.04) | —* |
| mRT-AVG (μM) | 0.84 (0.03) | 0.76 (0.05) |
| Stratus | | |
| cpNFLT-AVG (μM) | 0.92 (0.02) | 0.80 (0.05) |
| mRT-AVG (μM) | 0.84 (0.03) | 0.76 (0.05) |

Abbreviations:
AROC = area under the receiver operating curve;
SE = standard error;
the abbreviations of diagnostic parameters are the same as Table 2.
*The AROC was not generated because mGCCT-SID was not significant in the generalized estimating equation logistic regression model (P-value = 0.11)

What is claimed is:

1. A method for detecting optic neuropathy in a subject, comprising:
   (1) generating at least one initial map selected from the group consisting of a macular map centered on the fovea using optical coherence tomography (OCT), wherein said initial map consists of a raster or grid scanning pattern covering an area at least about 6 mm×6 mm for said macular map;
   (2) constructing a map of a ganglion cell complex thickness based on said initial map;
   (3) computing a derivative map from said map of ganglion cell complex thickness;
   (4) applying a statistical pattern analysis method to said map of ganglion cell complex thickness or said derivative map to detect abnormal areas, wherein said statistical pattern analysis method comprises a standard deviation comparison of a point-by-point comparison in which a data point having a predetermined percentage value above or below normal is identified as abnormal, said predetermined percentage value is selected from the range from about 0.5% to about 5%; and
   (5) determining one or more diagnostic parameters based on one or more of said map of ganglion cell complex thickness, derivative map, or detected abnormal areas;
   wherein said diagnostic parameter is two selected from focal loss volume (FLV), global loss volume (GLV), fractional deviation focal loss volume (FD_FLV), pattern deviation focal loss volume (PD_FLV), pattern coefficient of variation (PCV), or pattern cross-correlation (PCC), and
   wherein one or more of said diagnostic parameters, map of ganglion cell complex thickness or derivative map is used to diagnose and differentiate different types of optic neuropathies.

2. The method of claim 1, wherein said OCT is one selected from FD-OCT or TD-OCT.

3. The method of claim 1, wherein said scanning pattern is MM7 pattern.

4. The method of claim 1, wherein the step of constructing a map of retinal property comprises interpolating between the scan lines of the initial map to form a three dimensional model of the scanned area.

5. The method of claim 1, wherein the derivative map is one selected from deviation map (D), fractional deviation map (FD), or pattern deviation map (PD).

6. The method of claim 1, wherein said statistical method further includes one selected from overall average, superior average, inferior average, superior-inferior difference, root-mean-square, or a combination thereof.

7. The method of claim 1, wherein said predetermined range is about 5 percent.

8. The method of claim 1, wherein said optic neuropathy is one selected from glaucoma, optic neuritis, anterior ischemic optic neuropathy (AION), 9. The method of claim 1, further comprising a step of cross-correlating said ganglion cell complex_map or said derivative map of the subject to a reference map characteristic of a known optic neuropathy to determine at least one pattern cross-correlation parameter.

10. The method of claim 9, wherein a higher value of said cross-correlation parameter indicates a higher likelihood that said subject suffers from said known optic neuropathy.

11. A method for detecting and diagnosing glaucoma in a subject, comprising:
   obtaining a macular map of the subject using a non-invasive imaging technique, wherein said macular map is at least about 6 mm×6 mm obtained in a raster or grid scanning pattern;
   constructing a ganglion cell complex thickness map from said macular map;
   generating one or more derivative maps from said ganglion cell complex map;
   analyzing said ganglion cell complex thickness map, said one or more derivative maps, or both by applying a statistical pattern analysis method to said map of ganglion cell complex thickness or said derivative map to detect abnormal areas, wherein said statistical pattern analysis method comprises a standard deviation comparison of a point-by-point comparison in which a data point having a predetermined percentage value above or below normal is identified as abnormal, said predetermined percentage value is selected from the range from about 0.5% to about 5%;
   determining a value or values for one or more diagnostic parameters based on the ganglion cell complex map, the one or more derivative maps, the identified abnormal area, or a combination thereof, wherein said value or values are correlated to a diagnosis of glaucoma,
   wherein said diagnostic parameter is two selected from focal loss volume (FLV), global loss volume (GLV), fractional deviation focal loss volume (FD_FLV), pattern deviation focal loss volume (PD_FLV), pattern coefficient of variation (PCV), or pattern cross-correlation (PCC).

12. The method of claim 11, wherein said non-invasive imaging technique is FD-OCT.

13. A method of detecting and diagnosing optic neuropathy in a subject using optical coherence tomography, comprising:
   obtaining an optical coherence tomography image of said subject's macular or peripapillary region;
   generating a ganglion cell complex thickness map from said image;
   computing a derivative map from said ganglion cell complex thickness map, wherein said derivative map is computed by applying a mathematical transformation based on a normative reference;
   applying a statistical pattern analysis method to said derivative map to identify abnormal areas, wherein said statistical pattern analysis method comprises a standard deviation comparison of a point-by-point comparison in which a data point having a predetermined percentage value above or below normal is identified as abnormal, said predetermined percentage value is selected from the range from about 0.5% to about 5%; and determining one or more diagnostic parameter(s) based on said derivative map and result of said pattern analysis step, wherein said diagnostic parameter is two selected from focal loss volume (FLV), global loss volume (GLV), fractional deviation focal loss volume (FD_FLV), pattern deviation focal loss volume (PD_FLV), pattern coefficient of variation (PCV), or pattern cross-correlation (PCC).

14. The method of claim 13, wherein said derivative map is one selected from deviation map (D), fractional deviation map (FD), or pattern deviation map (PD).

15. A method of detecting and diagnosing glaucoma in a patient comprising the steps of:

generating a macular ganglion cell complex thickness map comprising ganglion cell complex thickness measurements in the macular region of the patient's retina using optical coherence tomography;

comparing said macular ganglion cell complex thickness map to a reference macular ganglion cell complex thickness map by applying a statistical pattern analysis method comprising a standard deviation comparison of a point-by-point comparison in which a data point having a predetermined percentage value above or below normal is identified as abnormal, said predetermined percentage value is selected from the range from about 0.5% to about 5%; and determining one or more diagnostic parameter(s) based on a result of said comparing step, wherein said macular ganglion cell complex thickness is defined by the combined thickness of the nerve fiber layer, the ganglion cell layer, and the inner plexiform layer of the retina, and wherein said diagnostic parameter is two selected from focal loss volume (FLV), global loss volume (GLV), fractional deviation focal loss volume (FD_FLV), pattern deviation focal loss volume (PD_FLV), pattern coefficient of variation (PCV), or pattern cross-correlation (PCC).

* * * * *